United States Patent
Fujii et al.

(10) Patent No.: US 10,139,402 B2
(45) Date of Patent: Nov. 27, 2018

(54) SEPARATION METHOD, DETECTION METHOD, SIGNAL MEASUREMENT METHOD, METHOD FOR DETERMINING DISEASE, METHOD FOR EVALUATING DRUG EFFICACY OF DISEASE TREATMENT DRUG, KIT, AND LIQUID COMPOSITION

(71) Applicants: JSR CORPORATION, Minato-ku (JP); JSR LIFE SCIENCES CORPORATION, Minato-ku (JP)

(72) Inventors: Hiroya Fujii, Minato-ku (JP); Motoaki Mizuuchi, Minato-ku (JP); Tetsuji Yamaguchi, Minato-ku (JP); Hiroki Abe, Minato-ku (JP)

(73) Assignees: JSR CORPORATION, Minato-ku (JP); JSR Life Sciences Corporation, Minato-ku (JP)

( * ) Notice: Subject to any disclaimer, the term of this patent is extended or adjusted under 35 U.S.C. 154(b) by 0 days.

(21) Appl. No.: 15/035,094

(22) PCT Filed: Nov. 6, 2014

(86) PCT No.: PCT/JP2014/079477
§ 371 (c)(1),
(2) Date: Aug. 15, 2016

(87) PCT Pub. No.: WO2015/068772
PCT Pub. Date: May 14, 2015

(65) Prior Publication Data
US 2016/0349246 A1 Dec. 1, 2016

Related U.S. Application Data

(60) Provisional application No. 61/968,967, filed on Mar. 21, 2014.

(30) Foreign Application Priority Data

Nov. 6, 2013 (JP) .................. 2013-230530

(51) Int. Cl.
*G01N 33/543* (2006.01)
*C12Q 1/6804* (2018.01)
*C12Q 1/68* (2018.01)

(52) U.S. Cl.
CPC ....... *G01N 33/5432* (2013.01); *C12Q 1/6804* (2013.01); *G01N 2800/52* (2013.01)

(58) Field of Classification Search
None
See application file for complete search history.

(56) References Cited

U.S. PATENT DOCUMENTS

| | | |
|---|---|---|
| 2009/0220944 A1 | 9/2009 | Fais et al. |
| 2012/0058492 A1 | 3/2012 | Lozupone et al. |
| 2012/0309018 A1 | 12/2012 | Skolnick et al. |
| 2013/0196355 A1 | 8/2013 | Fais et al. |
| 2014/0141986 A1 | 5/2014 | Spetzler et al. |
| 2014/0220580 A1 | 8/2014 | Brown et al. |

FOREIGN PATENT DOCUMENTS

| | | | |
|---|---|---|---|
| JP | 2011-510309 A | 3/2011 | |
| WO | 2009/092386 A2 | 7/2009 | |
| WO | 2010/065968 A1 | 6/2010 | |
| WO | WO 2012/115885 A1 * | 8/2012 | ............ C12Q 1/68 |
| WO | 2013/022995 A2 | 2/2013 | |

OTHER PUBLICATIONS

Douglas D. Taylor, et al., "MicroRNA signatures of tumor-derived exosomes as diagnostic biomarkers of ovarian cancer", Gynecologic Oncology, vol. 110, pp. 13-21, (2008).
Mariantonia Logozzi, et al., "High Levels of Exosomes Expressing CD63 and Caveolin-1 in Plasma of Melanoma Patients", PLOS One, vol. 4, No. 4, pp. 1-10, (Apr. 2009).
International Search Report dated Feb. 10, 2015 in PCT/JP14/079477 Filed Nov. 6, 2014.

* cited by examiner

*Primary Examiner* — Nancy J Leith
(74) *Attorney, Agent, or Firm* — Oblon, McClelland, Maier & Neustadt, L.L.P.

(57) ABSTRACT

A method for separating a vesicle having a lipid bilayer membrane from a biological sample, includes forming a complex of a vesicle and a solid phase carrier by bringing the biological sample containing the vesicle having the lipid bilayer membrane into contact with the solid phase carrier to which a ligand for recognizing a surface antigen present on a surface of the vesicle is bound. The complex is washed. The forming is performed in the presence of a nonionic surfactant which does not comprise an aromatic group to reduce an aggregation of the complex.

8 Claims, 11 Drawing Sheets

NEGATIVE USING (a) PHOSPHOTUNGSTIC ACID OR (b) URANYL ACETATE

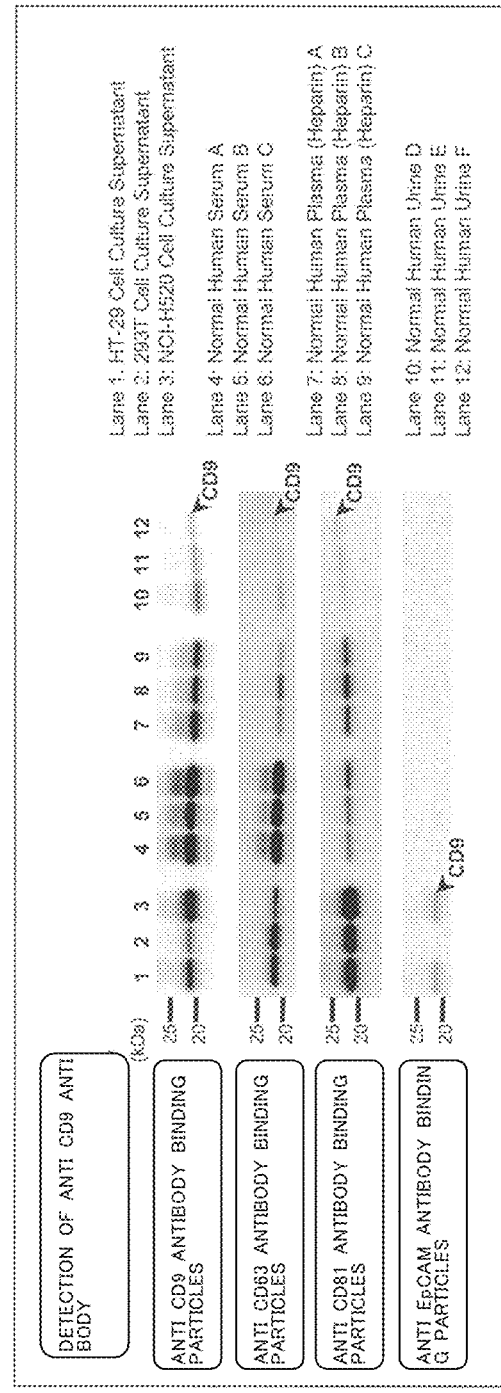

SEPARATION METHOD, DETECTION METHOD, SIGNAL MEASUREMENT METHOD, METHOD FOR DETERMINING DISEASE, METHOD FOR EVALUATING DRUG EFFICACY OF DISEASE TREATMENT DRUG, KIT, AND LIQUID COMPOSITION

TECHNICAL FIELD

The present invention relates to a separation method, a detection method, a signal measurement method, a method for determining a disease, a method for evaluating drug efficacy of a drug for disease treatment, a kit, and a liquid composition. More specifically, it relates to a method for separating a vesicle having a lipid bilayer membrane such as an exosome, a method for detecting nucleic acids or proteins by using the separation method, a signal measurement method, a method for determining a disease, a method for evaluating drug efficacy of a drug for disease treatment, a kit for determining a disease or evaluating drug efficacy, and a liquid composition used for the separation method.

BACKGROUND ART

A vesicle has a structure covered with a lipid bilayer membrane, and among such vesicles, an exosome is known as a vesicular granule which is present in body fluid of a living organism. Similar to a common cell surface, it is known that various membrane proteins are present on a surface of an exosome. Meanwhile, it is also found that microRNA (miRNA) is contained in the inside of an exosome in addition to various proteins such as cytokine.

It is also known that an exosome is secreted from various cells such as cells of an immune system or various cancer cells. Attention is given to the function of an exosome as a mediator for intercellular communication in a living organism and also to the relationship between an exosome and a physiological phenomenon or a disease such as cancer, and therefore a study thereto currently being made. For example, it has been already reported that, when an antibody of EpCAM as a cancer marker is used, an exosome is separated from circulating blood of a patient with ovarian cancer and a relationship is found between an expression amount of miRNA derived from exosome and progress of ovarian cancer (Non Patent Literature 1).

As a 4 transmembrane membrane protein expressed on an exosome, there are CD9, CD63 and CD81 belonging to tetraspanin family, and it has been reported in Non Patent Literature 2 that the amount of exosome is higher in plasma from a patient with melanoma compared to that of a healthy person, and it can be detected and quantified by an antibody against CD63 or an antibody against Caveolin-1 as a cancer-related marker. Furthermore, by combining and reacting a plasma sample after centrifuge with CD63 antibody or an antibody against various membrane proteins or the like, a signal derived from an exosome of a cancer patient is quantified and analyzed (Patent Literature 1).

CITATION LIST

Patent Literature

Patent Literature 1: WO 2010/065968 A

Non Patent Literature

Non Patent Literature 1: D. D. Taylor, et al., Gynecol. Oncol., 110, 13-21 (2008)

Non Patent Literature 2: M. Logozzi, et al., PLoS ONE., 4, 1-10 (2009)

SUMMARY OF INVENTION

Technical Problem

Meanwhile, as a function of a reaction solution or a washing solution for a solid phase carrier conjugated with an antibody or a buffer for suspending antibody binding particles, it is required to have a function of reducing non-specific adsorption on a reaction vessel such as plate or particle surface, or reducing particle aggregation occurring during the reaction.

However, when a vesicle covered with a lipid bilayer membrane such as an exosome is captured with particles like magnetic particles, not only the non-specific adsorption easily occurs but also the particle aggregation is easily caused, and thus there are cases in which the recovery rate of vesicles or particle washing efficiency is adversely affected by them. When the antibody binding particles after the reaction are insufficiently washed, a problem arises that purification rate of an exosome is lowered due to incorporation of contaminating proteins that are derived from a test sample.

For such reasons, even for a case of separating a vesicle covered with a lipid bilayer membrane, it is required to have a buffer which can reduce the non-specific adsorption on a solid phase carrier and particle aggregation and to have high washing performance.

However, it found that, even when a particle storing buffer or a reaction buffer is added with a protein such as BSA that is generally used to suppress the non-specific adsorption or particle aggregation, particle aggregation is caused at the time of separating vesicles covered with a lipid bilayer membrane, and an influence is exhibited on, for example, proteome analysis of a purified exosome which is additionally performed thereafter.

It is also required to have less disruption of a vesicle having a lipid bilayer membrane at the time of separating a vesicle covered with lipid bilayer membrane.

The problem to be solved by the present invention is to provide a method for separating a vesicle having a lipid bilayer membrane, in which the method has excellent removal efficiency of impurity and hardly causes disruption of a vesicle having a lipid bilayer membrane.

Solution to Problem

Accordingly, the inventors of the present invention conducted intensive studies, and as a result, with regard to a method for separating a vesicle having a lipid bilayer membrane including a complex forming step for forming a complex of a vesicle and a solid phase carrier by bringing a biological sample including the vesicle having the lipid bilayer membrane into contact with the solid phase carrier to which a ligand for recognizing a surface antigen present on a surface of the vesicle is bound and a washing step for washing the complex, the aforementioned problem can be solved if at least any of the complex forming step and the washing step is performed in the presence of a nonionic surfactant. The present invention has been completed accordingly.

That is, according to the present invention, there is provided <1> a method for separating a vesicle having a lipid bilayer membrane including: a complex forming step for forming a complex of a vesicle and a solid phase carrier by bringing a biological sample including the vesicle having the lipid bilayer membrane into contact with the solid phase carrier to which a ligand for recognizing a surface antigen present on a surface of the vesicle and is bound, a washing step for washing the complex, in which at least any of the complex forming step and the washing step is performed in the presence of a nonionic surfactant.

According to the present invention, there is provided <2> a method for detecting a nucleic acid in a vesicle, further including a nucleic acid detecting step for detecting the nucleic acid in the vesicle after the separation method according to <1> described above.

Further, according to the present invention, there is provided <3> a method for detecting a protein derived from a vesicle, further including a protein detecting step for detecting a protein present at least one of inside or on a surface of a vesicle after the separation method according to <1> described above.

Further, according to the present invention, there is provided <4> a method for measuring a signal derived from a vesicle, further including a signal measuring step for measuring an intensity of a signal derived from a vesicle formed to have the complex after the separation method according to <1> described above.

Further, according to the present invention, there is provided <5> a method for determining an onset of a disease in a test subject, including a step for measuring, based on the signal measurement method according to <4> described above, an intensity of a signal derived from a vesicle formed to have the complex by using a biological sample derived from the test subject.

Further, according to the present invention, there is provided <6> a method for evaluating drug efficacy of a drug for treating a disease, including a step for measuring, based on the signal measurement method according to <4> described above, an intensity of a signal derived from a vesicle formed to have the complex by using a biological sample derived from the test subject before and after an administration of a drug for treating a disease.

Further, according to the present invention, there is provided <7> a kit including a solid phase carrier bound with a ligand which recognizes a surface antigen present on a surface of a vesicle having a lipid bilayer membrane, and a liquid composition including a nonionic surfactant.

Further, according to the present invention, there is provided <8> a liquid composition for washing a complex which is used for a method for separating a vesicle having a lipid bilayer membrane including a complex forming step for forming a complex of a vesicle and a solid phase carrier by bringing a biological sample including the vesicle having the lipid bilayer membrane into contact with the solid phase carrier to which a ligand for recognizing a surface antigen present on a surface of the vesicle is bound and a washing step for washing the complex, in which the liquid composition includes a nonionic surfactant.

Advantageous Effects of Invention

The method for separating a vesicle having a lipid bilayer membrane of the present invention has excellent removal efficiency of impurity and is unlikely to cause disruption of a vesicle having a lipid bilayer membrane.

Furthermore, when the kit or liquid composition of the present invention is used for separation of a vesicle having a lipid bilayer membrane, impurities are sufficiently removed and it is unlikely to have disruption of a vesicle having a lipid bilayer membrane

BRIEF DESCRIPTION OF DRAWINGS

FIG. 11 is a Western blot image illustrating that the surface proteins derived from a vesicle captured by antibody binding magnetic particles can be detected from various culture supernatant and body fluid.

DESCRIPTION OF EMBODIMENTS

Figure 1:
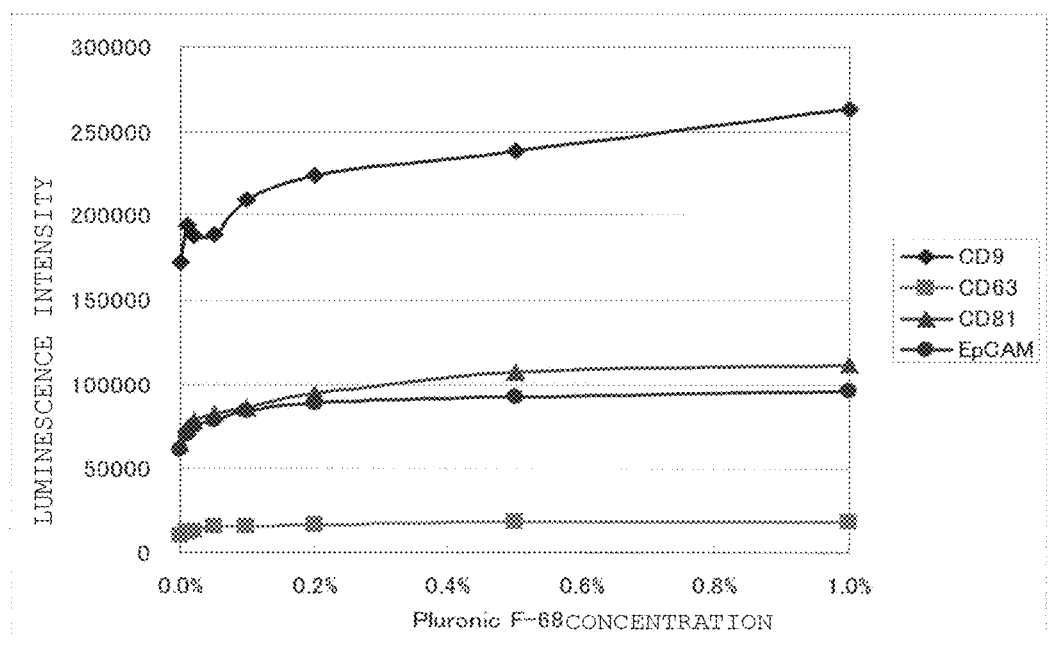
FIG. 1 is a graph illustrating the influence of a nonionic surfactant on the reaction between an antibody bound to a particle and an exosome.

[Method for Separating Vesicle Having Lipid Bilayer Membrane]

The method for separating a vesicle having a lipid bilayer membrane according to the present invention is characterized in that it includes a complex forming step for forming a complex of a vesicle and a solid phase carrier by bringing a biological sample including the vesicle having the lipid bilayer membrane into contact with the solid phase carrier to which a ligand for recognizing a surface antigen present on a surface of the vesicle is bound and a washing step for washing the complex, in which at least any of the complex forming step and the washing step is performed in the presence of a nonionic surfactant.

(Nonionic Surfactant)

The nonionic surfactant used for the separation method of the present invention preferably does not contain an aromatic group in the molecule. By using a nonionic surfactant not containing such aromatic group in the molecule, non-specific adsorption of impurities on a solid phase carrier can be suppressed without causing disruption of a lipid bilayer membrane which constitutes a vesicle such as exosome. Furthermore, the reactivity of a capturing reaction between a vesicle and a solid phase carrier is enhanced. Furthermore, the influence of a purified exosome on proteome analysis or the like can be suppressed.

Examples of the nonionic surfactant not containing an aromatic group in the molecule include a polyethylene glycol type nonionic surfactant and a polyhydric alcohol type nonionic surfactant having a hydrophobic group added to polyalcohol such as glycerol and pentaerythritol.

The polyethylene glycol type nonionic surfactant is not particularly limited, as long as it has a polyethylene oxide chain as a hydrophilic group, and examples thereof include a polyalkylene glycol ethylene oxide adduct, a polyhydric alcohol fatty acid ester ethylene oxide adduct, a higher alcohol ethylene oxide adduct, a fatty acid ethylene oxide adduct, a higher alkylamineethylene oxide adduct, a fatty acid amide ethylene oxide adduct, and an ethylene oxide adduct of fat or oil. Among them, from the viewpoint of having the effect of reducing non-specific adsorption or exhibiting less damage on a vesicle, a polyalkylene glycol ethylene oxide adduct and a polyhydric alcohol fatty acid ester ethylene oxide adduct are preferable.

The polyalkylene glycol ethylene oxide adduct is preferably a block copolymer type, and preferred examples thereof include a block copolymer having a block consisting of polyethylene oxide (hereinbelow, also referred to as block A) and a block consisting of polyalkylene oxide and having 3 or more carbon atoms in the alkylene (hereinbelow, also referred to as block B). Furthermore, the carbon atom number of the alkyleneoxy group contained in the block B is preferably 3 to 6, more preferably 3 or 4, and particularly preferably 3. Meanwhile, the copolymer having carbon atom number of 3 for the alkyleneoxy group contained in the block B corresponds to a polypropylene glycol ethylene oxide adduct.

Furthermore, the total content of the block A is preferably 15 to 99% by mass, more preferably 50 to 99% by mass, even more preferably 60 to 95% by mass, and particularly preferably 70 to 90% by mass in the block copolymer.

Furthermore, the total content of the block B is, from the viewpoint of cell toxicity, preferably 1 to 85% by mass, more preferably 1 to 50% by mass, even more preferably 5 to 40% by mass, and particularly preferably 10 to 30% by mass in the block copolymer.

Meanwhile, those contents can be measured by, for example, NMR, and if there are 2 or more block A, the content means the total of each content of two or more block A. Similarly, if there are 2 or more block B, the content means the total of each content of two or more block B.

Among those polyalkylene glycol ethylene oxide adducts, an ABA type triblock copolymer having a structure in which the block B is inserted between two blocks A is preferable, as exemplified by PLURONIC®.

Examples of a commercially available product of a polyalkylene glycol ethylene oxide adduct include PLURONIC® F-68 and PLURONIC® L-62 (all manufactured by ADEKA).

Furthermore, as the aforementioned polyhydric alcohol fatty acid ester ethylene oxide adduct, an ethylene oxide adduct of fatty acid ester and an ethylene oxide adduct of sorbitol fatty acid ester are preferable. An ethylene oxide adduct of sorbitan fatty acid ester is more preferable.

Furthermore, the "fatty acid" in the polyhydric alcohol fatty acid ester ethylene oxide adduct may be any of unsaturated fatty acid and saturated fatty acid. Furthermore, the fatty acid may be either linear or branch, and it is preferably linear. Carbon atom number of the fatty acid is preferably 8 to 18, more preferably 10 to 20, and even more preferably 12 to 18. More specific examples thereof include lauric acid, palmitic acid, stearic acid, and oleic acid.

Examples of a commercially available product of a polyhydric alcohol fatty acid ester ethylene oxide adduct include TWEEN® 20, TWEEN® 40, TWEEN® 60, TWEEN® 65, TWEEN® 80, and TWEEN® 85 (all manufactured by Wako Pure Chemical Industries, Ltd.).

Furthermore, examples of the polyhydric alcohol type nonionic surfactant having a hydrophobic group added to polyhydric alcohol include fatty acid ester of glycerol, fatty acid ester of pentaerythritol, fatty acid ester of sorbitol or sorbitan, fatty acid ester of sucrose, alkyl ether of polyhydric alcohol, and fatty acid amide of alkanol amines. Among them, preferred are those having fatty acid residue as a hydrophobic group. Meanwhile, the fatty acid residue is preferably the same as the fatty acid residue which is contained in the aforementioned polyhydric alcohol fatty acid ester ethylene oxide adduct.

Among those containing fatty acid residues, fatty acid ester of sorbitol or sorbitan is preferable, and sorbitan fatty acid ester is more preferable.

Furthermore, among the above nonionic surfactants not containing an aromatic group in the molecule, from the viewpoint of having the effect of reducing non-specific adsorption or exhibiting less damage on a vesicle, a polyethylene glycol type nonionic surfactant is preferable, a polyalkylene glycol ethylene oxide adduct and a polyhydric alcohol fatty acid ester ethylene oxide adduct are more preferable, and a polyalkylene glycol ethylene oxide adduct is even more preferable.

Meanwhile, the nonionic surfactant may be used either singly or in combination of two or more thereof.

Furthermore, the HLB (Hydrophile-Lipophile Balance) value of the nonionic surfactant other than the polyalkylene glycol ethylene oxide adduct is preferably 13.1 or more, and more preferably 13.5 or more.

Meanwhile, as described herein, the HLB value refers to Hydrophile-Lipophile Balance by Griffin, and it is a value representing the degree of affinity of a surfactant for water or oil. For example, TWEEN® 20 has HLB value of 16.7 and TWEEN® 80 has HLB value of 15.0. Furthermore, as a nonionic surfactant containing an aromatic group, TRITON™ X-100 has HLB value of 13.5 and NONIDET® P-40 has HLB value of 13.1.

Furthermore, the weight average molecular weight of the nonionic surfactant is preferably 500 to 50000, more preferably 1000 to 30000, and even more preferably 2000 to 20000 from the viewpoint of cell toxicity.

Meanwhile, the weight average molecular weight can be measured by liquid chromatography, NMR, or MALDI-TOF/MS or the like.

Concentration of the nonionic surfactant is, in terms of final concentration, preferably 0.005% (w/v) or more, more preferably 0.01% (w/v) or more, even more preferably 0.015% (w/v) or more, and particularly preferably 0.02% (w/v) or more, and preferably 10% (w/v) or less, more preferably 5% (w/v) or less, even more preferably 3.5% (w/v) or less, and particularly preferably 2% (w/v) or less relative to the total amount of a liquid phase in the system (amount excluding solid content such as solid phase carrier from the entire volume of a biological sample or a buffer or the like). Meanwhile, the above final concentration is preferable for any of the complex forming step and washing step.

When the concentration of the nonionic surfactant falls within the above numerical value range, an excellent effect of reducing non-specific adsorption is acquired. In a case in which the solid phase carrier is a particle, an excellent effect of preventing aggregation is acquired. Furthermore, the binding between a ligand and a surface antigen is not inhibited.

According to the present invention, any one of the complex forming step and washing step may be performed in the presence of a nonionic surfactant, or both of the complex forming step and washing step may be performed in the presence of a nonionic surfactant. Furthermore, it is also possible that, before the complex forming step, a composition such as buffer containing a nonionic surfactant is added in advance to a biological sample, and the resultant is used.

Specifically, in a case in which the solid phase carrier has a shape such as plate or fiber shape that is not dispersed in liquid phase, the nonionic surfactant may be added, as in the form of liquid phase for the complex forming step or washing solution used for the washing step, to a system. Furthermore, in a case in which the solid phase carrier is dispersed in a liquid phase in the form of particle such as magnetic particle, it is preferable that the carrier is used after being added in advance to a particle dispersion before addition to a biological sample as a test sample, or it is added to a buffer for preparing a biological sample or to a washing solution used for the washing step or the like.

For example, by adding a nonionic surfactant to a storing buffer for antibody binding particles, the dispersibility of a particulate solid phase carrier can be enhanced compared to BSA or other polymers, and also the aggregation and non-specific adsorption onto a storage vessel or a reaction vessel can be suppressed. Furthermore, by adding a nonionic surfactant to a washing buffer, adsorption of non-specific components derived from a test sample can be suppressed without disrupting an animal cell or a vesicle such as exosome, and even in a case in which a nonionic surfactant not containing an aromatic group in the molecule is used, the washing performance of antibody binding particles can be increased to the same level as TRITON™ X-100, which is a nonionic surfactant containing an aromatic group.

(Complex Forming Step)

The complex forming step is a step for forming a complex between a vesicle and a solid phase carrier by bringing a biological sample including the vesicle having a lipid bilayer membrane into contact with the solid phase carrier to which a ligand for recognizing a surface antigen present on a surface of the vesicle is bound. According to the contact, a vesicle is captured by a ligand, and a complex of a vesicle and a solid phase carrier is formed.

Meanwhile, in a reaction system for the complex forming step, a ligand recognizing a surface antigen, which is present on a surface of the vesicle having a lipid bilayer membrane, may be also present in addition to the ligand bound to the solid phase carrier.

The biological sample is not particularly limited, as long as it contains a vesicle having a lipid bilayer membrane, and examples thereof include various liquids such as body fluid, bacterial liquid, cell culture medium, cell culture supernatant, and liquid containing disrupted tissue cells. Among them, body fluid and cell culture supernatant are preferable. Examples of the body fluid include components of blood composition such as whole blood, blood serum, blood plasma, blood components, various blood cells, blood clot, and blood platelet, and also urine, semen, milk, sweat, interstitial fluid, interstitial lymph, bone marrow fluid, tissue fluid, saliva, gastric juice, joint fluid, pleural fluid, bile acid, ascite, and amniotic fluid. Preferably, it is components of blood composition or urine. According to the separation method of the present invention, a vesicle can be separated selectively and efficiently from a wide variety of biological samples. For example, even when blood plasma or blood serum is used as a biological sample, it is unlikely to have non-specific adsorption.

Meanwhile, the components of blood composition may be those treated with an anti-clotting agent such as citric acid, heparin, or EDTA.

The biological sample may be used as a pre-treated sample after being added in advance to a buffer composition containing a nonionic surfactant. Alternatively, the sample as such collected from a living organism may be used. Namely, according to the separation method of the present invention, a simple and selective separation can be made without performing a pre-treatment based on an isolation method or the like using PEG precipitation or ultracentrifuge or the like.

Furthermore, although examples of the vesicle having a lipid bilayer membrane include a cell and a vesicle such as an exosome which is discharged extracellularly from a cell, the separation method of the present invention is particularly preferably used for a case in which the vesicle is an exosome. In general, when the solid phase carrier has a particle shape such as magnetic particles, there may be a case in which impurities are difficult to be removed by washing as the particles are easily aggregated and it becomes difficult to have re-dispersion of the particles when an exosome is captured by using an antibody bound to the particles. However, according to the present invention, the aggregation among particles can be suppressed by adding a nonionic surfactant.

Furthermore, the surface antigen present on a surface of a vesicle is not particularly limited as long as it is a material with antigenicity, which is present on a vesicle surface. Examples of the surface antigen of an exosome include tetraspanins such as CD9, CD63, or CD81; proteins related to antigen-presentation such as MHCI or MHCII; adhesion molecules such as integrin, ICAM-1, or EpCAM; cytokine such as EGFRvIII or TGF-β/cytokine receptors, and enzymes. Among them, the antigen protein present on a surface of an exosome is preferable.

Furthermore, the used amount of the above biological sample is, in terms of the final concentration, preferably 1 to 900 (w/v), and more preferably 10 to 50% (w/v) relative to the total amount of liquid phase in the system (an amount excluding a solid content such as solid phase carrier from the entire volume of a biological sample or a buffer).

Furthermore, the solid phase carrier used for the separation method of the present invention is not particularly limited, as long as it is bound with a ligand which recognizes a surface antigen present on a surface of a vesicle.

As for the ligand, an antibody recognizing a surface antigen present on a surface of a vesicle is preferable. More preferably, it is an antibody recognizing an antigen protein which is present on a surface of an exosome. Furthermore, it may be either a monoclonal antibody or a polyclonal antibody, and a monoclonal antibody is preferable.

The monoclonal antibody is not particularly limited, and it may be an antibody produced in accordance with a known method, for example, a method described in K. Watanabe et al., Vasohibin as an endothelium-derived negative feedback regulator of angiogenesis, J. Clin. Invest. 114 (2004), 898-907. Furthermore, the monoclonal antibody recognizing tetraspanins such as surface antigen CD9, CD63, or CD81 of an exosome may be prepared in view of WO 2013/099925 A.

Meanwhile, examples of the aforementioned antibody class include IgG and IgM, and it is preferably IgG. Furthermore, a fragment obtained by preparing them as a small molecule may be also used, and examples thereof include F(ab')2, Fab', and Fab.

A quality of material of the solid phase carrier for binding the above ligand include, for example, a high molecular compound such as polystyrenes, polyethylenes, polypropylenes, polyesters, poly(meth)acrylonitriles, a styrene-butadiene copolymer, poly(meth)acrylic acid esters, a fluororesin, cross-linked dextran, or polysaccharide; glass; metal; magnetic material; a resin composition containing a magnetic material; and a combination thereof.

Furthermore, shape of the solid phase carrier is not particularly limited, and examples thereof include a tray, a globule, a particle, a fiber, a rod, a dish, a container, a cell, a micro plate, and a test tube.

In the present invention, from the viewpoint of easiness in solid-liquid separation or washing, the magnetic particles are preferable.

Examples of the magnetic particles include a metal such as ferric oxide ($Fe_3O_4$), maghemite ($\gamma$-$Fe_2O_3$), various ferrites, iron, manganese, nickel, cobalt and chrome; magnetic fine particles consisting of an alloy of cobalt, nickel, or manganese; and magnetic particles containing those magnetic materials in a resin. Examples of the resin include a hydrophobic polymer and a hydrophilic polymer.

Among them, magnetic particles containing a magnetic material in a resin are preferable, and those obtained by forming a polymer layer on a surface of parent particles containing superparamagnetic fine particles are more preferable. Examples thereof include magnetic particles described in JP 2008-32411 A that are obtained by forming a hydrophobic first polymer layer on a surface of parent particles containing superparamagnetic fine particles, forming a second polymer layer having a glycidyl group at least on a surface of the first polymer layer, and introducing a polar group therein by chemical modification of the glycidyl group.

Representative examples of the superparamagnetic fine particles include fine particles of iron oxide with particle diameter of 20 nm or less (preferably, particle diameter of 5 to 20 nm), and examples thereof include ferrite expressed by $XFe_2O_4$ (X=Mn, Co, Ni, Mg, Cu, $Li_{0.5}Fe_{0.5}$ or the like), magnetite expressed by $Fe_3O_4$, and $\gamma$-$Fe_2O_3$. From the viewpoint of having strong saturation magnetization and little residual magnetization, it is preferable to contain any one of $\gamma$-$Fe_2O_3$ and $Fe_3O_4$.

Furthermore, the monomer for forming the above hydrophobic first polymer layer is classified into a monofunctional monomer and a crosslinkable monomer.

Examples of the monofunctional monomer include aromatic vinyl monomers such as styrene, $\alpha$-methyl styrene, or halogenated styrene; and ethylenically unsaturated carboxylic acid alkyl ester monomer such as methyl acrylate, methyl methacrylate, ethyl acrylate, ethyl methacrylate, stearyl acrylate, stearyl methacrylate, cyclohexylacrylate, cyclohexyl methacrylate, isobornyl acrylate, or isobornyl methacrylate.

Furthermore, examples of the crosslinkable monomer include a polyfunctional (meth)acrylate such as ethylene glycol diacrylate, ethylene glycol dimethacrylate, trimethylol propane triacrylate, trimethylol propane trimethacrylate, pentaerythritol triacrylate, pentaerythritol trimethacrylate, dipentaerythritol hexaacrylate, or dipentaerythritol hexamethacrylate; conjugated diolefins such as butadiene or isoprene, and divinyl benzene, diallyl phthalate, allyl acrylate, and allyl methacrylate.

Furthermore, the monomer for forming the second polymer layer is mainly intended to introduce a functional group to a surface of particle, and it includes a monomer containing a glycidyl group. Content of the monomer containing a glycidyl group is preferably 20% by mass or more in the monomer for forming the second polymer layer. Examples of the copolymerizable monomer containing a glycidyl group include glycidyl acrylate, glycidyl methacrylate, and allyl glycidyl ether.

The polar group to be introduced by chemical modification of a glycidyl group in the second polymer layer is preferably a functional group which can react with a ligand, and it is more preferably a group containing at least one atom selected from a group consisting of an oxygen atom, a nitrogen atom, and a sulfur atom. Among them, an amino group, an aldehyde group, a carboxy group, and an active ester group are more preferable. In particular, when the second polymer layer of magnetic particles includes the above polar group and a 2,3-dihydroxypropyl group, a good binding property with a ligand is acquired.

As a method for binding a ligand to a solid phase carrier, it includes a physical adsorption method and a chemical binding method such as a covalent bond method and an ionic bond method. Examples of the physical adsorption method include a method in which a ligand is directly bound to a solid phase carrier and a method in which it is chemically bound to other protein such as albumin followed by fixing based on adsorption. Examples of the chemical binding method include a method in which direct binding to a solid phase carrier is performed by using a functional group introduced to a surface of a solid phase carrier, in which the functional group is capable of reacting with a ligand, a method of carrying out binding after introduction of a spacer molecule (for example, carbodiimide compound) between a solid phase carrier and a ligand by chemical binding, and a method of binding a ligand to other protein such as albumin followed by chemical binding of the protein to a solid phase carrier.

Furthermore, the used amount of the solid phase carrier bound with a ligand is, in terms of the final concentration, preferably 0.005 to 5% (w/v), and more preferably 0.01 to 1% (w/v) relative to the total amount of a liquid phase in the system (amount excluding solid content such as solid phase carrier from the entire volume of a biological sample or a buffer or the like).

The complex forming step may be performed by using, if necessary, salts, proteins such as albumin, or a surfactant other than the aforementioned nonionic surfactant in addition to each component described above. However, considering the analysis at later stage, it is preferable not to use a protein or a nucleic acid.

The reaction temperature for the complex forming step is generally in the range of 2 to 42° C. The reaction time is generally 5 minutes to 24 hours. When the reaction is performed at 2 to 8° C., the reaction time is preferably about 8 to 30 hours. When the reaction is performed at room temperature (20° C.) to 42° C., the reaction time is preferably about 5 to 60 minutes.

The pH in the system during the complex forming step is not particularly limited. It is preferably in the range of pH 5 to 10, and more preferably in the range of pH 6 to 8. In order to maintain a desired pH, a buffer solution is generally used, and examples thereof include a phosphate buffer solution, a tris(hydroxymethyl)aminomethane buffer solution, a HEPES buffer solution, and an MES buffer solution.

(Washing Step)

The washing step is a step for washing a complex of a vesicle and a solid phase carrier which has been formed in the above complex forming step. According to the step, unreacted components or unreacted labeling materials or the like are removed. Also, a system containing the complex of the complex forming step may be directly washed.

The washing step is generally classified into two types depending on the shape of a solid phase carrier. When the solid phase carrier has a particle shape like magnetic particles, a method of washing after dispersing magnetic particles in a washing solution can be exemplified. Meanwhile, if the solid phase carrier has a shape like micro plate, a method of washing after contacting the surface thereof with a washing solution can be exemplified. For any of those embodiments, it is preferable in the present invention to use, as a washing solution, a washing solution containing a nonionic surfactant which does not include the aforementioned aromatic group in the molecule.

Furthermore, when the solid phase carrier is a magnetic particle, the washing step preferably includes a magnetic collecting step for collecting the magnetic particles by magnetic force and separating the magnetic particles from a liquid phase, and a dispersing step for dispersing the magnetic particles that are separated by the magnetic collecting step, in a washing solution. Accordingly, unreacted substances or impurities in a biological sample can be more efficiently washed and separated, and removed from a surface of magnetic particles.

Specifically, it may be performed by applying magnetic field to a reaction vessel to have magnetic particles adhered on a wall of the reaction vessel, removing the reaction supernatant, and if necessary, adding a washing solution, and repeating an operation of applying magnetic field and removing the supernatant.

The washing solution is preferably a washing solution which contains a nonionic surfactant not containing an aromatic group in the molecule, and a buffer solution described in the above complex forming step. pH of the washing solution is preferably in the range of pH 5 to 10, and more preferably in the range of pH 6 to 8. Specific examples thereof include TBS containing 0.01% nonionic surfactant.

(Dissociating Step)

The separation method of the present invention may also include, after the aforementioned washing step, a dissociating step for dissociating a captured vesicle from a ligand.

As for the condition for having dissociation of a specific bond based on an antigen/antibody reaction, for a case in which the ligand is a specific antibody, various conditions have been known for affinity chromatography (see, for example, "Affinity Chromatography Principles & Methods" Pharmacia LKB Biotechnology), for example. The dissociating step can be performed in accordance with it. Namely, examples of a dissociating solution which is used in the present invention include an acidic solution such as hydrochloric acid, sulfuric acid, propionic acid, acetic acid, and glycine/hydrochloric acid buffer; an alkali solution such as aqueous sodium hydroxide solution, aqueous potassium hydroxide solution, aqueous ammonia solution, and diethyl amine; a high ionic strength solution such as 3 M aqueous solution of sodium chloride and 4.5 M aqueous solution of magnesium chloride; a solution containing a surfactant such as SDS, TRITON™ X-100, and TWEEN® 20; a buffer solution containing a substance for lowering polarity such as dioxane and ethylene glycol; and a buffer solution containing urea or guanidine hydrochloride or the like, in addition to chaotropic ions such as trichloroacetic acid and thiocyanide acid.

[Method for Detecting Nucleic Acid and Method for Detecting Protein]

The method for detecting a nucleic acid in a vesicle of the present invention further includes a nucleic acid detecting step for detecting a nucleic acid in a vesicle after the aforementioned separation method.

Furthermore, the method for detecting a protein derived from a vesicle of the present invention further includes a protein detecting step for detecting a protein present at least one of inside or on a surface of a vesicle after the aforementioned separation method.

Those detection methods can be performed in accordance with a normal method except performing the aforementioned separation method. When the vesicle having a lipid bilayer membrane is an exosome, a nucleic acid or a protein can be detected from a recovered exosome by a known method such as PCR method, electrophoretic method, Western blot method, and immunochemical method. Furthermore, examples of the nucleic acid include miRNA and mRNA.

In particular, as the exosome is secreted from various cells, for example, cells of an immune system or various cancer cells, nucleic acid (miRNA, in particular) derived from an exosome can be detected by the nucleic acid detection method of the present invention, and by the analysis, a physiological phenomenon or various diseases can be determined.

[Method for Signal Measurement]

The method for measuring a signal derived from a vesicle of the present invention further includes, after the separation method, a signal measuring step for measuring an intensity of a signal derived from a vesicle formed to have the complex.

The method for signal detection can be carried out by an immunological measurement method, and examples thereof include an enzyme immunoassay (EIA), enzyme linked immunosorbent assay (ELISA), fluorescent immunoassay (FIA), radioactive immunoassay (RIA), luminescence immunoassay, an immuno blotting method, and a Western blot method. From the viewpoint of detecting an antibody conveniently and with good sensitivity, an ELISA method is preferable. Examples of the ELISA method include a competition method and a sandwich method.

Herein, an exemplary separation method for the case of using a sandwich ELISA method is described. First, a ligand recognizing a surface antigen present on a vesicle surface is allowed to bind to a solid phase carrier, and by contacting it with a biological sample containing a vesicle having a lipid bilayer membrane, a complex is formed followed by washing. By further adding a monoclonal antibody or an antibody fragment thereof, a disease-specific membrane protein antibody, or a labeled antibody modified with the antibody thereof, an additional complex is formed. Furthermore, by detecting a label amount in a formed complex, the amount of a signal derived from a vesicle contained in the biological sample or the amount of a disease-specific vesicle contained in the biological sample can be measured.

[Method for Disease Determination]

The method of the present invention for determining an onset of a disease in a test subject is characterized in that it includes a step for measuring, by using a biological sample derived from a test subject, an intensity of a signal derived from a vesicle formed to have the complex based on the signal measurement method described above (hereinbelow, also referred to as the step (I)).

Furthermore, when the signal intensity measured in the step (I) is compared to the signal intensity of a biological sample derived from a control and the signal intensity from the test subject is recognized to be stronger than the signal intensity from a control, it can be determined that there is an onset of a disease in the test subject (hereinbelow, also referred to as the step (II)).

Examples of the disease which can be determined by the disease determination method of the present invention include a cancer disease (for example, colon cancer, breast cancer, endometrial cancer, cervical cancer, ovarian cancer, pancreas cancer, stomach cancer, esophageal cancer, liver cancer, lung cancer, kidney cancer, or skin cancer), an inflammation system related disease (for example, rheumatism, arthrosis deformans, kidney disease, pancreas disease, hepatitis, allergic response), neurodegenerative disease such as Alzheimer disease, a brain disease, a disease related with immunodeficiency, infertility, depression, a mental disease such as autism, an intractable disease such as Parkinson's disease, an autoimmune disease, a circulatory system disease, a blood disease, a digestive system disease, a senile disease, and an inflammatory disease. Among them, it is useful for determination of a cancer disease and a disease of an immunological system, and it is particularly useful for determination of a cancer disease.

Furthermore, when applied to an index of immune activity of cytotoxic T cell (CTL), it can be used for determination of an effect of a cancer vaccine on a cancer disease.

The step (I) can be performed by a normal method, except performing the measurement by the aforementioned signal measurement method.

Furthermore, in the step (II), comparison is made by performing a statistical analysis based on a signal of a biological sample derived from a control with reference to signal intensity measured in the step (I). The analysis method is not particularly limited, and a known method can be used. Furthermore, as for the determination thereafter, if a signal of a biological sample derived from a test subject is stronger than a signal from a control, it is determined that there is a high possibility of having an onset of a disease. Meanwhile, in the present invention, the control means an average person who belongs to the same age group with the same sex as the test subject and exhibits no onset of a disease. The signal intensity from a control can be measured at the same time with the signal intensity from a test subject, or a statistical value obtained from the values that have been separately measured in advance can be used.

[Method for Evaluating Drug Efficacy of Drug for Treating Disease]

The method for evaluating drug efficacy of a drug for treating a disease of the present invention is characterized in that it includes a step for measuring, by using a biological sample derived from a test subject before and after an administration of a drug for treating a disease, an intensity of a signal derived from a vesicle formed to have the complex based on the signal measurement method described above (hereinbelow, also referred to as the step (A)).

Furthermore, when the signal intensity derived from a complex in a biological sample which is derived from a test subject after administration of a drug for disease treatment is recognized to be weaker than the signal intensity derived from a complex in a biological sample which is derived from a test subject before administration of a drug for disease treatment, it can be determined that drug efficacy is most likely to be exhibited by the drug for disease treatment (hereinbelow, also referred to as the step (B)).

Examples of the drug for disease treatment include a drug for treating a disease that can be determined by the aforementioned determination method. Specific examples of the preferred drug include an anti-cancer drug and a drug for an anti-immunological system related disease.

The step (A) can be performed by a normal method, except performing a measurement by the aforementioned signal measurement method.

Furthermore, in the step (B), comparison is made by performing a statistical analysis based on a signal of a biological sample before administration of a drug for disease treatment with reference to signal intensity measured in the step (A). The analysis method is not particularly limited, and a known method can be used. Furthermore, as for the determination thereafter, if a signal amount of a biological sample after administration of a drug for disease treatment is less than a signal amount of a biological sample before administration of a drug for disease treatment, it is determined that the drug is highly such asly to exhibit an effect of inhibiting the disease.

In particular, since an exosome is secreted from cells of an immune system or various cancer cells, it is believed that, by measuring a change in blood exosome before and after the administration of a drug (including a change in the amount of membrane protein in addition to the increase/decrease in the content), drug efficacy in a patient can be evaluated. Furthermore, when a ligand for a membrane protein which is specific to a cancer cell is combined with a ligand for a surface antigen of an exosome, it is expected that specificity of cancer diagnosis is improved or identification of cancer type can be made, and thus development of a diagnostic drug more specific to a cancer disease can be achieved.

[Kit]

The kit of the present invention is characterized in that it includes a solid phase carrier bound with a ligand which recognizes a surface antigen present on a surface of a vesicle having a lipid bilayer membrane, and a liquid composition containing a nonionic surfactant. Such kit is useful for the aforementioned separation method, determination of a disease, and evaluation of drug efficacy of a drug for treating a disease.

The solid phase carrier and nonionic surfactant to be contained in a liquid composition may be the same as those used for the above separation method. Concentration of the nonionic surfactant is, relative to the entire amount of the liquid composition, preferably 0.005 to 10% (w/v), and more preferably 0.02 to 2% (w/v). Furthermore, pH of the liquid composition is, although not particularly limited, preferably in the range of pH 5 to 10, and more preferably in the range of pH 6 to 8. In order to maintain a desired pH, a buffer solution is generally used, and examples thereof include a phosphate buffer solution, a tris(hydroxymethyl) aminomethane buffer solution, a HEPES buffer solution, and an MES buffer solution.

[Liquid Composition]

The liquid composition of the present invention is a liquid composition for, washing a complex which is used for a method for separating a vesicle having a lipid bilayer membrane including a complex forming step for forming a complex of a vesicle and a solid phase carrier by bringing a biological sample including the vesicle having the lipid bilayer membrane into contact with the solid phase carrier to which a ligand for recognizing a surface antigen present on a surface of the vesicle is bound, and a washing step for washing the complex, in which it contains a nonionic surfactant.

Composition and pH of the liquid composition of the present invention are the same as those of the liquid composition included in the kit of the present invention.

The liquid composition of the present invention is used for the separation method of the present invention.

EXAMPLES

Hereinbelow, the present invention is described in detail in view of examples, but the present invention is not limited to those examples.

Test Example 1—Test for Confirming Aggregation (1)

First, as a control buffer, tris buffered saline (TBS, pH 7.4) was prepared, and as a buffer of Example 1, TBS (pH 7.4) added with a nonionic surfactant (tripolyoxyethylene (160) polyoxypropylene (30) PLURONIC® F-68 (ADEKA, the same applies hereinafter)) to have concentration of 0.1% (w/v) was prepared.

Subsequently, to each of above buffers, anti CD63 antibody binding magnetic particles (Exosome-Dynabeads Human CD63 Isolation/Detection, Ref 10606D, manufactured by Life technologies) were added to have concentration of 0.1% (w/v). Then, 100 µL of this particle storing buffer and 100 µL of culture supernatant of HT29 cells (100× concentrate was diluted by a factor of 5 with TBS) containing exosome were added to a 1.5 mL tube followed by mixing. It was shaken for 1 hour at 25° C. Then, an aggregate of the antibody binding magnetic particles which is adhered on an inner wall surface of the tube was visually confirmed. The results are shown in Table 1.

TABLE 1

|  | Composition of buffer | Aggregate of particles |
| --- | --- | --- |
| Control | TBS | + |
| Example 1 | 0.1% (w/v) PLURONIC ® F68, TBS | − |

+: Aggregate of particles was confirmed, −: Aggregate of particles was not confirmed.

As shown in Table 1, when magnetic particles are suspended in TBS only (control), adhesion of the aggregate of magnetic particles on an inner wall surface was confirmed. However, when the magnetic particles are suspended after adding 0.1% (w/v) nonionic surfactant in TBS (Example 1), adhesion of the aggregate was not confirmed.

Test Example 2—Test for Confirming Aggregation (2)

First, as a control buffer, TBS (pH 7.4) was prepared, and as a buffer of Examples 2 to 7, TBS (pH 7.4) added with a nonionic surfactant (tripolyoxyethylene (160) polyoxypropylene (30) glycol PLURONIC® F-68) to have concentration shown in Table 2 below was prepared. Furthermore, as a buffer of Comparative Examples 1 and 2, TBS (pH 7.4) added with bovine serum albumin (BSA) to have concentration shown in Table 2 below was prepared.

Subsequently, to each of above buffers, magnetic particles (manufactured by JSR Life Sciences Corporation MS300/Carboxyl, the same applies hereinafter) bound with anti EpCAM antibody (manufactured by JSR Life Sciences Corporation, the same applies hereinafter) were added to have concentration of 0.2 (w/v). Then, 100 µL of this particle storing buffer and 100 µL of culture supernatant of HT29 cells (100 times the concentrated solution was diluted by a factor of 5 with TBS) containing exosome were added to a 1.5 mL tube followed by mixing. It was shaken for 1 hour at 25° C. Then, an aggregate of the antibody binding magnetic particles which is adhered on an inner wall surface of the tube was visually confirmed. The results are shown in Table 2.

TABLE 2

|  | Composition of buffer | Aggregate of particles |
| --- | --- | --- |
| Control | TBS | + |
| Comparative Example 1 | 0.1% (w/v) BSA, TBS | + |
| Comparative Example 2 | 1.0% (w/v) BSA, TBS | + |
| Example 2 | 0.02% (w/v) PLURONIC ® F68, TBS | − |
| Example 3 | 0.05% (w/v) PLURONIC ® F68, TBS | − |
| Example 4 | 0.1% (w/v) PLURONIC ® F68, TBS | − |
| Example 5 | 0.2% (w/v) PLURONIC ® F68, TBS | − |
| Example 6 | 0.5% (w/v) PLURONIC ® F68, TBS | − |
| Example 7 | 1.0% (w/v) PLURONIC ® F68, TBS | − |

+: Aggregate of particles was confirmed, −: Aggregate of particles was not confirmed.

As shown in Table 2, even for the anti EpCAM antibody binding magnetic particles, the aggregate of the magnetic particles was confirmed to be adhered on the wall surface when they are suspended in TBS only (control). In addition, the aggregation was not reduced even after adding BSA (Comparative Examples 1 and 2).

Meanwhile, when suspension is performed after adding 0.02 to 1.0% (w/v) nonionic surfactant to TBS (Examples 2 to 7), no adhesion of aggregates was confirmed.

Meanwhile, a test was performed in the same manner as the above Test Example 2, except that anti EpCAM antibody is changed to anti CD9 antibody (manufactured by Abcam plc., ab2215, the same applies hereinafter) or anti CD63 antibody (manufactured by JSR Life Sciences Corporation, the same applies hereinafter). As a result, the same results as those of Test Example 2 were obtained.

Test Example 3—Influence of Addition of Nonionic Surfactant on Reaction

To a 96 well white plate (manufactured by Corning Incorporated), (i) TBS containing 0.05% (w/v) magnetic particles (manufactured by JSR Life Sciences Corporation MS300/Carboxyl) that are bound with anti CD9 antibody, anti CD63 antibody, anti CD81 antibody or anti EpCAM antibody and 1.0% (w/v) nonionic surfactant (PLURONIC® F-68), (ii) MES solution (1 µg/mL) of an antibody, that is, the same antibody as above (i) except that it is labeled with an alkali phosphatase, and (iii) culture supernatant of HT29 cells (100 times the concentrated solution was diluted by a factor of 100 with TBS) were added, each in amount of 25 µL, followed by mixing. The resultant was shaken for 20 minutes at 25° C., and while conducting magnetic collecting, the antibody binding magnetic particles after the reaction were washed with the washing buffer (TBS containing 0.01% (w/v) TWEEN® 20). Then, 50 µL of a luminescent substrate (LUMIPULSE® substrate solution) was added thereto, and after 5 minutes, the luminescence intensity was measured by using a luminescence measuring device (GLO-MAX®, manufactured by Promega).

Furthermore, for the particle storing buffer which has been obtained by changing the concentration of a nonionic surfactant (PLURONIC® F-68) in the particle suspension (i) above from 1.00 (w/v) to 0% (w/v), 0.01% (w/v), 0.020 (w/v), 0.05% (w/v), 0.1% (w/v), 0.2% (w/v), or 0.5% (w/v), the luminescence intensity was measured in the same manner as above.

The results are illustrated in FIG. 1.

As illustrated in FIG. 1, even when the particle storing buffer is added with nonionic surfactant (PLURONIC® F-68) at 0.01 to 1.0% (w/v) (final concentration of 0.0033 to 0.33% (w/v)), the reaction between four of the antibody bound to magnetic particles and the exosome was not inhibited.

Test Example 4—Test for Determining Washing Performance

When the antibody binding magnetic particles are reacted with a test sample (blood serum, blood plasma, and urine), non-specific adsorption derived from the test sample was not sufficiently reduced by particle washing which uses TBS (pH 7.4) only, and it was confirmed by silver staining of SDS-PAGE. Since the non-specific adsorption was particularly high when blood serum was used, the washing performance of a particle washing buffer containing a nonionic surfactant was determined in the following order by using blood serum.

First, 150 µL of TBS (pH 7.4) containing 0.1% (w/v) magnetic particles (manufactured by JSR Life Sciences Corporation MS300/Carboxyl) that are bound with anti CD9 antibody, anti CD63 antibody, anti CD81 antibody or anti EpCAM antibody and 0.1% (w/v) nonionic surfactant (PLURONIC® F-68) and 150 µL of blood serum from a healthy person were added to a 1.5 mL tube followed by mixing.

The resultant was shaken for 1 hour at 25° C., and then the blood serum was removed by magnetic collecting. It was then washed 2 times with 0.5 mL of the washing buffer ((i) TBS, (ii) TBS containing 0.01% (w/v) TRITON™ X-100, or (iii) TBS containing 0.01% (w/v) PLURONIC® F-68).

Subsequently, it was subjected to magnetic collecting and the washing solution was discarded. Then, the antibody binding magnetic particles were suspended in 20 µL of 1× sample buffer (NUPAGE® LDS Sample Buffer (4×), Invitrogen Cat no. NP0008, the same applies hereinafter), and allowed stand for 5 minutes at 95° C. The entire amount was applied to SDS-PAGE, and silver staining (manufactured by (Cosmo Bio Co., Ltd.) was performed. The results are illustrated in FIG. 2.

Figure 2:
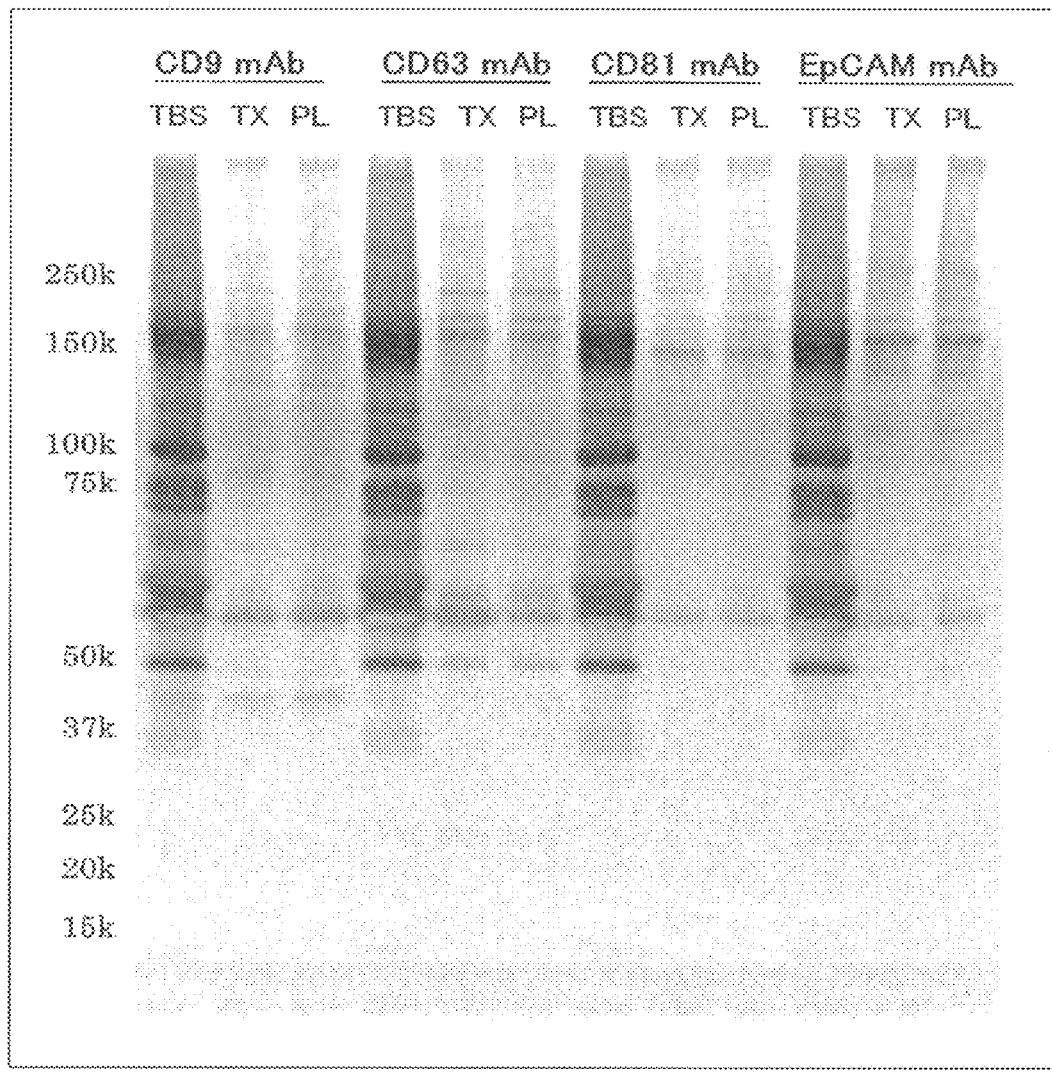
FIG. 2 is a silver-stained image illustrating the washing performance of a washing buffer containing a nonionic surfactant.

As illustrated in FIG. 2, in washing by TBS only (FIG. 2: lane TBS), the non-specific adsorption in which a large amount of the components derived from blood serum are adsorbed onto the particles was found for all four of anti-body binding the magnetic particles. However, by adding a 0.01% (w/v) nonionic surfactant (PLURONIC® F-68 or TRITON™ X-100) to the washing buffer (FIG. 2: lane PL, lane TX), the non-specific adsorption was remarkably reduced.

Meanwhile, since the nonionic surfactant not containing an aromatic group in the molecules (PLURONIC® F-68) exhibits only little influence on a lipid bilayer membrane, such nonionic surfactant not containing an aromatic group in the molecule is expected to be most suitable, in particular.

Test Example 5—Influence of Washing Buffer Containing Nonionic Surfactant on Specific Binding In order to confirm whether or not even the antigen (exosome) that specifically reacted with antibody binding magnetic particles is not released from the antibody by an action of the washing buffer containing the nonionic surfactant (PLURONIC® F-68), in addition to the adsorption of non-specific components derived from a test sample, the protein detection based on Western blot analysis was performed in the following order.

First, 100 µL of TBS (pH 7.4) containing 0.1% (w/v) magnetic particles (manufactured by JSR Life Sciences Corporation MS300/Carboxyl) that are bound with anti CD9 antibody, anti CD63 antibody, anti CD81 antibody or anti EpCAM antibody and 0.1% (w/v) nonionic surfactant (PLURONIC® F-68) and 100 µL of culture supernatant of HT29 cells (100 times the concentrated solution was diluted by a factor of 10 with TBS) containing exosome were added to a 1.5 mL tube followed by mixing.

The resultant was shaken for 1 hour at 25° C., and then the culture supernatant was removed by magnetic collecting. It was then washed 3 times with 0.5 mL of the washing buffer ((i) PBS containing 0.1% (w/v) BSA or (ii) TBS containing 0.01% (w/v) nonionic surfactant (PLURONIC® F-68)).

Subsequently, it was subjected to magnetic collecting and the washing solution was discarded. The antibody binding magnetic particles were suspended in 20 µL of 1× sample buffer, and allowed stand for 5 minutes at 95° C. The entire amount (20 µL) of the sample obtained after washing each antibody binding magnetic particles with each washing buffer was applied and subjected to SDS-PAGE. The gel was transferred to a PVDF membrane (TRANS-BLOT® TURBO™ Transfer Pack Midi format, 0.2 µm PVDF (BIO-RAD, Control 400072019)), and then shaken for 2 hours at 37° C. with the blocking buffer (TBS containing 1% (w/v) BSA and 0.1% (w/v) TWEEN® 20). The resultant was washed with the washing buffer (TBS containing 0.1% (w/v) TWEEN® 20), and reacted with a solution (solvent: TBS containing 0.5% (w/v) BSA) containing 1 µg/mL of anti CD81 antibody (Clone M38, Abnova MAB6435) as a primary antibody and a solution (solvent: TBS containing 0.5% (w/v) BSA) containing 1 µg/mL of HRP labeled anti mouse IgG antibody (Mouse TRUEBLOT® ULTRA: Anti-Mouse IgG HRP, Rockland 18-8817-33) as a labeling antibody, each at 25° C. for 1 hour. It was then washed with the washing buffer (TBS containing 0.1% (w/v) TWEEN® 20), and reacted with a luminescent substrate (SUPERSIGNAL™ West Femto Maximum Sensitivity substrate, Thermo scientific Cat#34095). The Western bolt image was then determined by using a luminescence measuring device (LAS-3000, FUJIFILM). The results are illustrated in FIG. 3.

Figure 3:
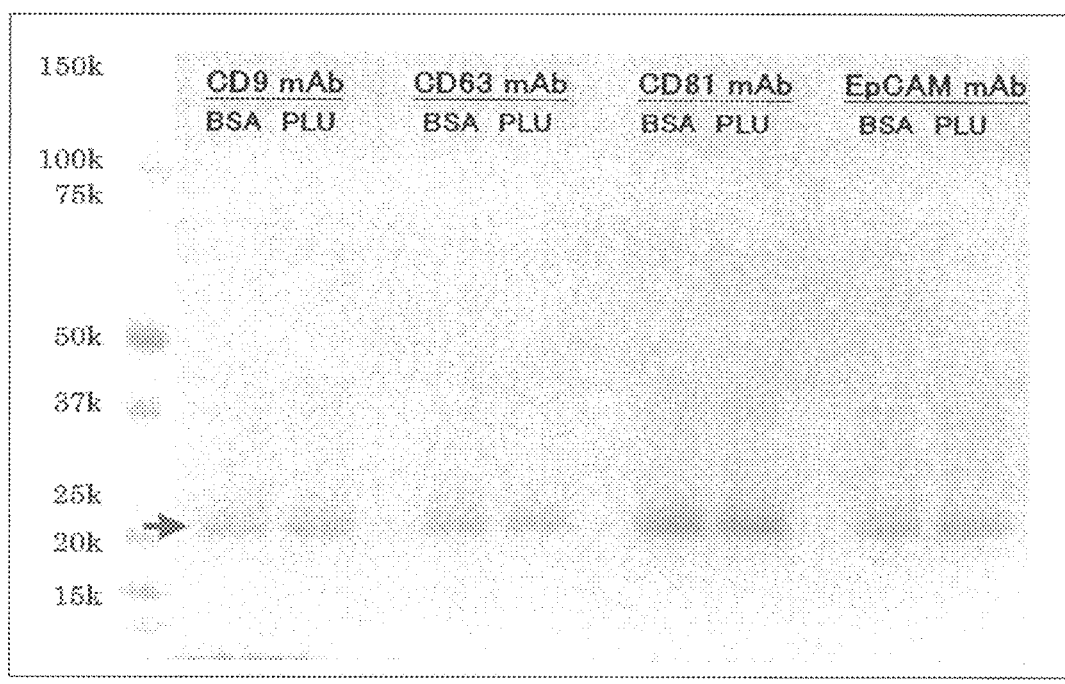
FIG. 3 is a Western blot image illustrating that the exosome is difficult to be released from an antibody bound to a particle by a washing buffer containing a nonionic surfactant.

As illustrated in FIG. 3, even when the antibody binding magnetic particles after the reaction (anti CD9 antibody, anti CD63 antibody, anti CD81 antibody, anti EpCAM antibody) are washed with TBS containing 0.01% (w/v) nonionic surfactant (PLURONIC® F-68) (FIG. 3, lane PLU), the exosome was not released from the antibody compared to the washing in which PBS containing 0.1% BSA is used (FIG. 3, lane BSA).

Test Example 6—Stability Test

In order to determine the stability of an exosome even when a nonionic surfactant (PLURONIC® F-68) is included during the reaction or washing of an antibody binding magnetic particles, particle size distribution of the exosome was measured in the following order.

First, culture supernatant of HT29 cells (100 times the concentrated solution) was diluted by a factor of 10 (10× culture supernatant) with (i) TBS (pH 7.4) or (ii) TBS (pH 7.4) containing 0.1% (w/v) nonionic surfactant (PLURONIC® F-68), and stored for 3 days in a refrigerator. After that, the 10× culture supernatant was diluted by a factor of 100 with TBS and, by using NanoSight LM10 (manufactured by NANO SIGHT), particle size distribution of the exosome was determined.

Even when the exosome was stored in TBS containing 0.1% (w/v) nonionic surfactant (PLURONIC® F-68), no change was shown in the particle size distribution of exosome compared to the storage using TBS only. For such reasons, it believed that the exosome stability is not affected by an addition of a nonionic surfactant (PLURONIC® F-68) to the storing buffer and washing buffer for antibody binding magnetic particles.

Test Example 7—Nonionic Surfactant

In order to determine the influence of various nonionic surfactants shown in Table 3 on the reaction, the reactivity between the antibody binding magnetic particles and exosome in the presence of each nonionic surfactant was measured in the following order.

First, (i) 200 µL of TBS (pH 7.4) containing 0.05% (w/v) magnetic particles (manufactured by JSR Life Sciences Corporation MS300/Carboxyl) that are bound with anti CD81 antibody and 1.0% (w/v) nonionic surfactant shown in Table 3, or (ii) 200 µL of PBS containing 0.05% (w/v) magnetic particles (manufactured by JSR Life Sciences Corporation MS300/Carboxyl) that are bound with anti CD81 antibody and 0.1% (w/v) BSA, and 10 µL of culture supernatant of HT29 cells (100 times the concentrated solution was diluted by a factor of 10 with TBS) containing exosome were added to a 1.5 mL tube followed by mixing. The resultant was shaken for 1 hour at 25° C.

It was added in an amount of 50 µL to a 96 well white plate (manufactured by Corning Incorporated), and while conducting magnetic collecting, the antibody binding magnetic particles after the reaction were washed with the washing buffer (TBS containing 0.01% (w/v) TWEEN® 20). Then, 50 µL of MES solution (1 µg/mL) of the antibody, i.e., anti CD81 antibody labeled with alkali phosphatase, were added thereto followed by mixing.

The resultant was shaken for 20 minutes at 25° C. Thereafter, while conducting magnetic collecting, the antibody binding magnetic particles after the reaction were washed with the washing buffer (TBS containing 0.01% (w/v) TWEEN® 20). Then, 50 µL of a luminescent substrate (LUMIPULSE® substrate solution, manufactured by FUJIREBIO INC.) was added thereto, and after 5 minutes, the luminescence intensity was measured by using a luminescence measuring device (GLOMAX®, manufactured by Promega). The results are shown in Table 4.

As shown in Table 4, a decrease in the reactivity to the antibody binding magnetic particles due to exosome disruption was not found even when polyalkylene glycol ethylene oxide adduct (PLURONIC® F-68, PLURONIC® L-62) and fatty acid ester of sorbitan (TWEEN® 20, TWEEN® 80) are added. Meanwhile, in case of TRITON™ X-100 (HLB value of 13.5) and NONIDET® P-40 (HLB value of 13.1), which are a nonionic surfactant containing an aromatic group, a decrease in the reactivity that is believed to be caused by exosome disruption was found.

From the above, it believed that the exosome stability and the reactivity to antibody binding magnetic particles are not affected by an addition of a nonionic surfactant (not containing an aromatic group in the molecule) in the storing buffer and washing buffer used for antibody binding magnetic particles.

TABLE 3

| Nonionic surfactant | Example | Name |
| --- | --- | --- |
| Polyalkylene glycol ethylene oxide adduct | PLURONIC ® F68 | Polyoxyethylene (160) polyoxypropylene glycol (30) |
| | PLURONIC ® L62 | Polyoxyethylene (10) polyoxypropylene glycol (30) |
| Fatty acid ester of sorbitan | TWEEN ® 20 | Polyoxyethylene sorbitan monolaurate |
| | TWEEN ® 80 | Polyoxyethylene sorbitan monooleate |
| Containing aromatic group | TRITON ™ X-100 | Polyoxyethylene (10) octylphenyl ether |
| | NONIDET ® P-40 | Poly(oxyethylene) = octylphenyl ether |

TABLE 4

| Nonionic surfactant (—) buffer | | Luminescence intensity | |
| --- | --- | --- | --- |
| 0.1% BSA, PBS | | 338756 | |

| Nonionic surfactant (1.0%) | | Luminescence intensity | /0.1% BSA |
| --- | --- | --- | --- |
| Polyalkylene glycol ethylene oxide adduct | PLURONIC ® F68 | 356617 | 105% |
| | PLURONIC ® L62 | 323172 | 95% |
| Fatty acid ester of sorbitan | TWEEN ® 20 | 279268 | 82% |
| | TWEEN ® 80 | 316715 | 93% |
| Containing aromatic group | TRITON ™ X-100 | 77990 | 23% |
| | NONIDET ® P-40 | 60356 | 18% |

Test Example 8—Determination of Captured Vesicle

In order to confirm that the exosome captured by antibody binding magnetic particles is not disrupted, the particle diameter and shape of the exosome were determined in the following order by using a particle size distribution analyzer and a transmission electron microscope.

100 µL of TBS (pH 7.4) containing 0.1% (w/v) (in final concentration) magnetic particles (manufactured by JSR Life Sciences Corporation MS300/Carboxyl) that are bound with anti CD9 antibody, anti CD63 antibody, anti CD81 antibody or anti EpCAM antibody and 0.1% (w/v) nonionic surfactant (PLURONIC® F-68) and 100 µL of culture supernatant of HT29 cells containing exosome were added to a 1.5 mL tube followed by mixing. The resultant was shaken for 1 hour at 25° C., and then the culture supernatant was removed by magnetic collecting. It was then washed 3 times with 0.5 mL of the washing buffer (TBS containing 0.1% (w/v) PLURONIC® F-68).

Figure 4:
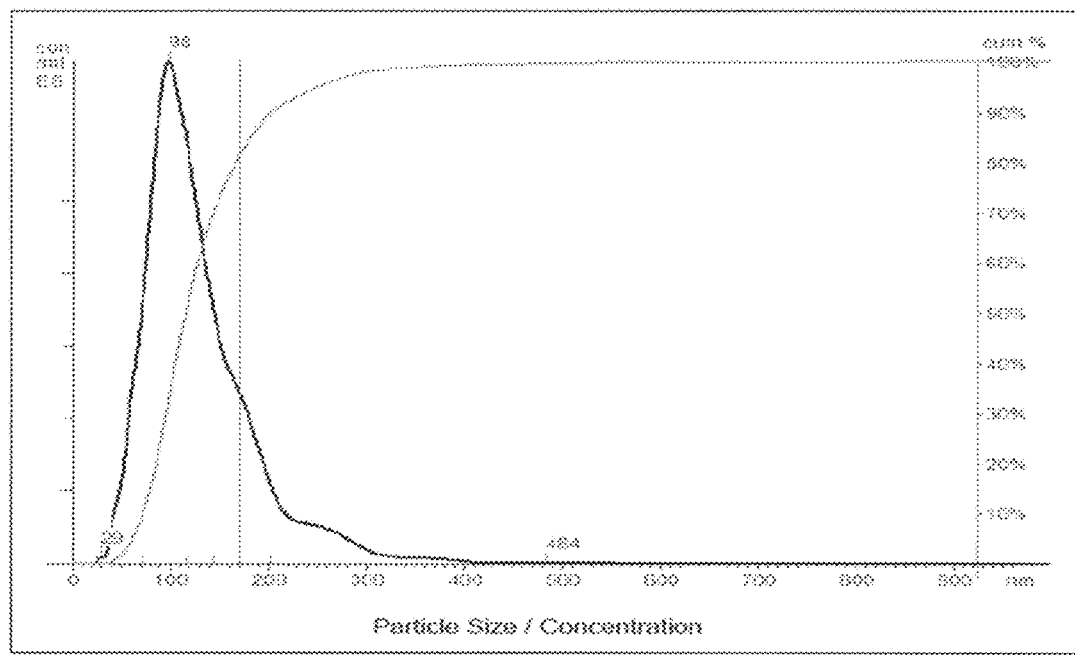
FIG. 4 is a wave form of particle size distribution illustrating that the exosome captured by magnetic particles bound with anti CD63 antibody has no problem in terms of particle diameter.
Figure 5:
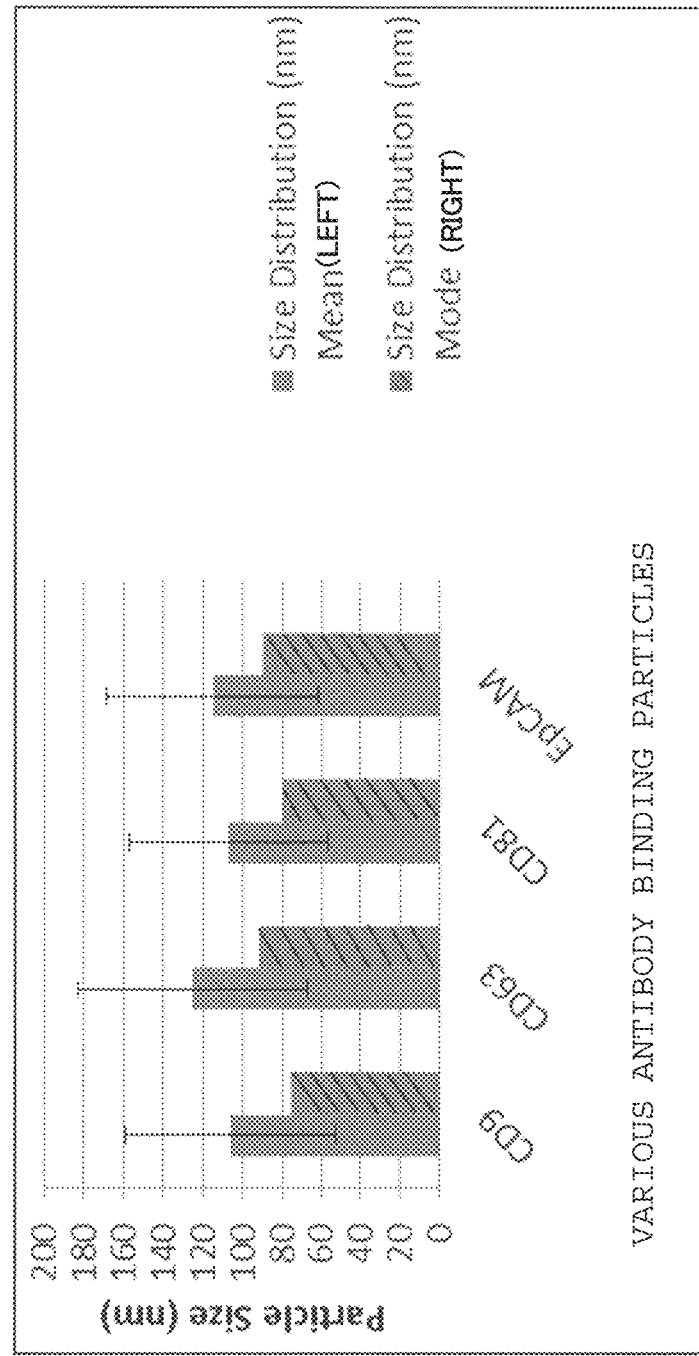
FIG. 5 is a graph of particle size distribution illustrating that the exosome captured by magnetic particles bound with each antibody has no problem in terms of particle diameter.

The washing buffer was removed by magnetic collecting, and by suspending the antibody binding magnetic particles in exosome elution buffer (manufactured by JSR Life Sciences Corporation, EXOCAP™ (trademark) Exosome Isolation and Enrichment Kits Exosome Elution Buffer), eluted exosome was prepared. After that, by using a nanoparticle analyzer, (NanoSight LM10, manufactured by NANO SIGHT), particle size distribution of the eluted exosome was determined. The results are illustrated in FIG. 4 and FIG. 5. FIG. 4 indicates the particle size distribution of the eluted exosome when anti CD63 antibody binding magnetic particles are used.

As a result, a waveform of the particle size distribution having a peak around 100 nm was found (FIG. 4). Furthermore, the same particle size distribution was found from all eluted exosomes which have been captured by the particles bound with anti CD9 antibody, anti CD63 antibody, anti CD81 antibody, or anti EpCAM antibody (FIG. 5).

By using the magnetic particles bound with anti CD9 antibody, the form of the eluted exosome which has been prepared in the same manner as above was directly observed under a transmission electron microscope. By using phosphotungstic acid or uranyl acetate, negative staining was performed. The results are illustrated in FIG. 6.

Figures 6A, 6B:
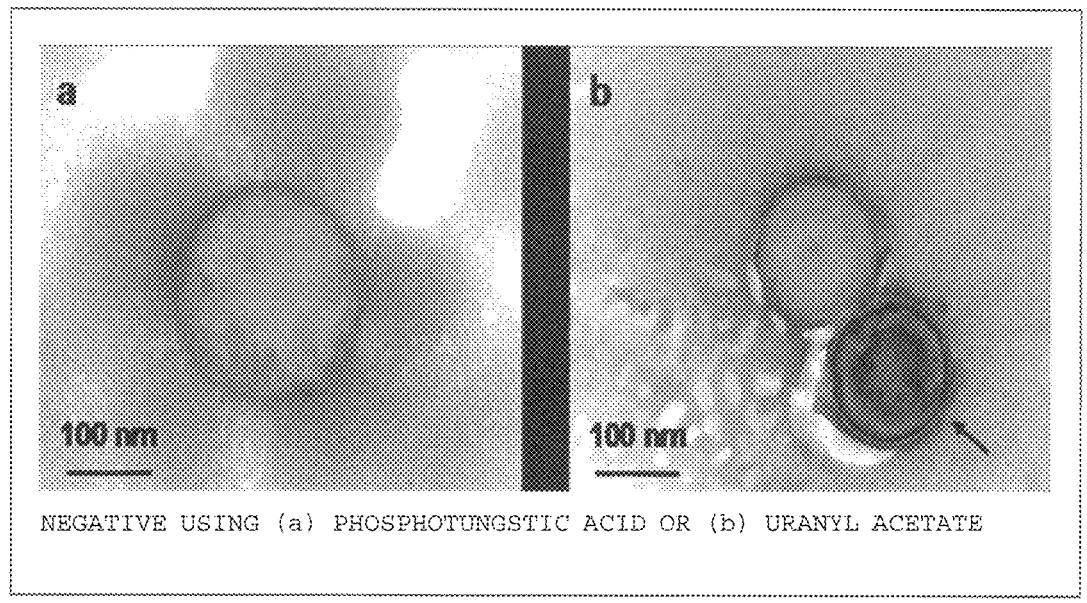
FIGS. 6A and 6B are an image of transmission type electron microscopy illustrating that the exosome captured by magnetic particles bound with anti CD9 antibody has no problem in terms of the form of exosome.

As a result, a vesicle-such as spherical structure (FIG. 6) and a lipid bilayer membrane of a vesicle were found (arrow in FIG. 6).

It believed from the above results that, since the vesicle captured by each antibody binding magnetic particle has a particle diameter of about 100 nm like the previously reported particle diameter of an exosome and the form is in excellent agreement with the observation result of a previous report, it is indeed an exosome and the exosome was not disrupted by the capturing step or the washing step.

Test Example 9—Detection of Nucleic Acid in Vesicle

Nucleic acid (total RNA) in a vesicle captured by antibody binding magnetic particles was detected by using a microchip type electrophoretic device. As for the standard exosome used as a sample, an exosome was separated from culture supernatant of HT29 cells by ultracentrifuge, and after adjusting it with PBS, it was subjected to protein quantification (BIO-RAD DC Protein Assay). Specific order is as described below. 100 μL of TBS (pH 7.4) containing 0.1% (w/v) (in final concentration) magnetic particles (manufactured by JSR Life Sciences Corporation MS300/Carboxyl) that are bound with anti CD9 antibody, anti CD63 antibody, anti CD81 antibody or anti EpCAM antibody and 0.1% (w/v) nonionic surfactant (PLURONIC® F-68) and 100 μL of PBS containing the standard exosome (0 μg, 1 μg, 3 μg, or 10 μg) were added to a 1.5 mL tube followed by mixing. The resultant was shaken for about 18 hours at 4° C., and then the unreacted exosome was removed by magnetic collecting. It was then washed 3 times with 1 mL of the washing buffer (TBS containing 0.1% (w/v) PLURONIC® F-68) followed by magnetic collecting for removal of the washing buffer.

From the exosome captured by antibody binding magnetic particles, total RNA was extracted by using RIP-Assay Kit for microRNA (manufactured by MBL, with reference to 2-step method) and then adjusted with RNase-free water.

Total RNA from the exosome captured by the antibody binding magnetic particles was detected by using a microchip type electrophoretic bioanalyzer (manufactured by Agilent Technologies). The results are illustrated in FIG. 7.

Figure 7:
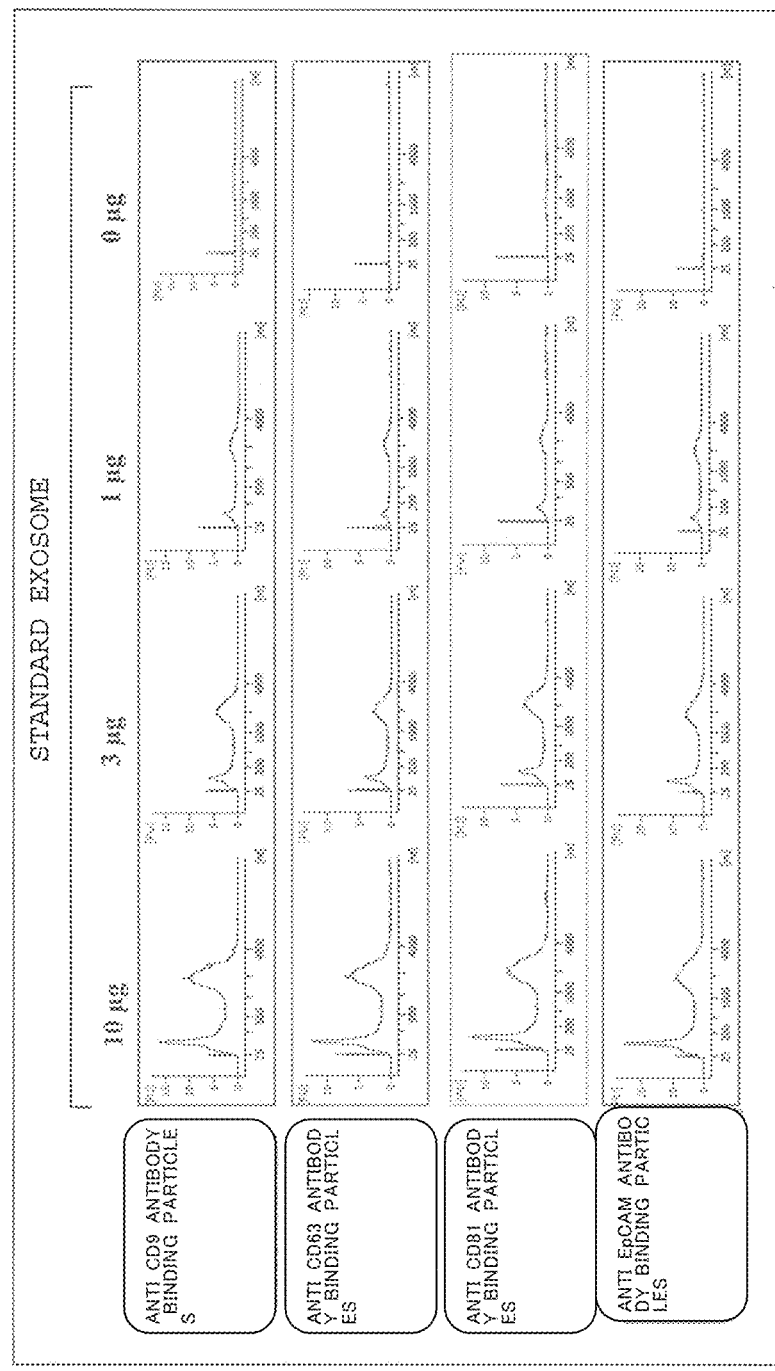
FIG. 7 is an analytical image of a bio analyzer illustrating that nucleic acids can be detected from the exosome that is captured by antibody binding magnetic particles.

As illustrated in FIG. 7, peaks of Small RNA and mRNA were found. Furthermore, the amount of the detected nucleic acid has increased in proportion to the amount of the standard exosome.

Test Example 10—Detection of MicroRNA in Vesicle

Nucleic acid (microRNA) in a vesicle captured by antibody binding magnetic particles was detected in the following order by using a quantitative PCR method.

First, the total RNA was extracted in the same manner as Test Example 9, except that, as antibody binding magnetic particles, (i) anti CD63 antibody binding magnetic particles, or (ii) a mixture of anti CD9 antibody binding magnetic particles, anti CD63 antibody binding magnetic particles, anti CD81 antibody binding magnetic particles, and anti EpCAM antibody binding magnetic particles (mass ratio of 1:1:1:1) is used, each in final particle concentration of 0.1% (w/v). Subsequently, by using MISCRIPT™ II RT kit (manufactued by QIAGEN) and MISCRIPT™ SYBR® Green PCR kit (manufactued by QIAGEN), quantification of microRNA (let-7a-1) was carried out. The results are illustrated in FIG. 8.

Figure 8:
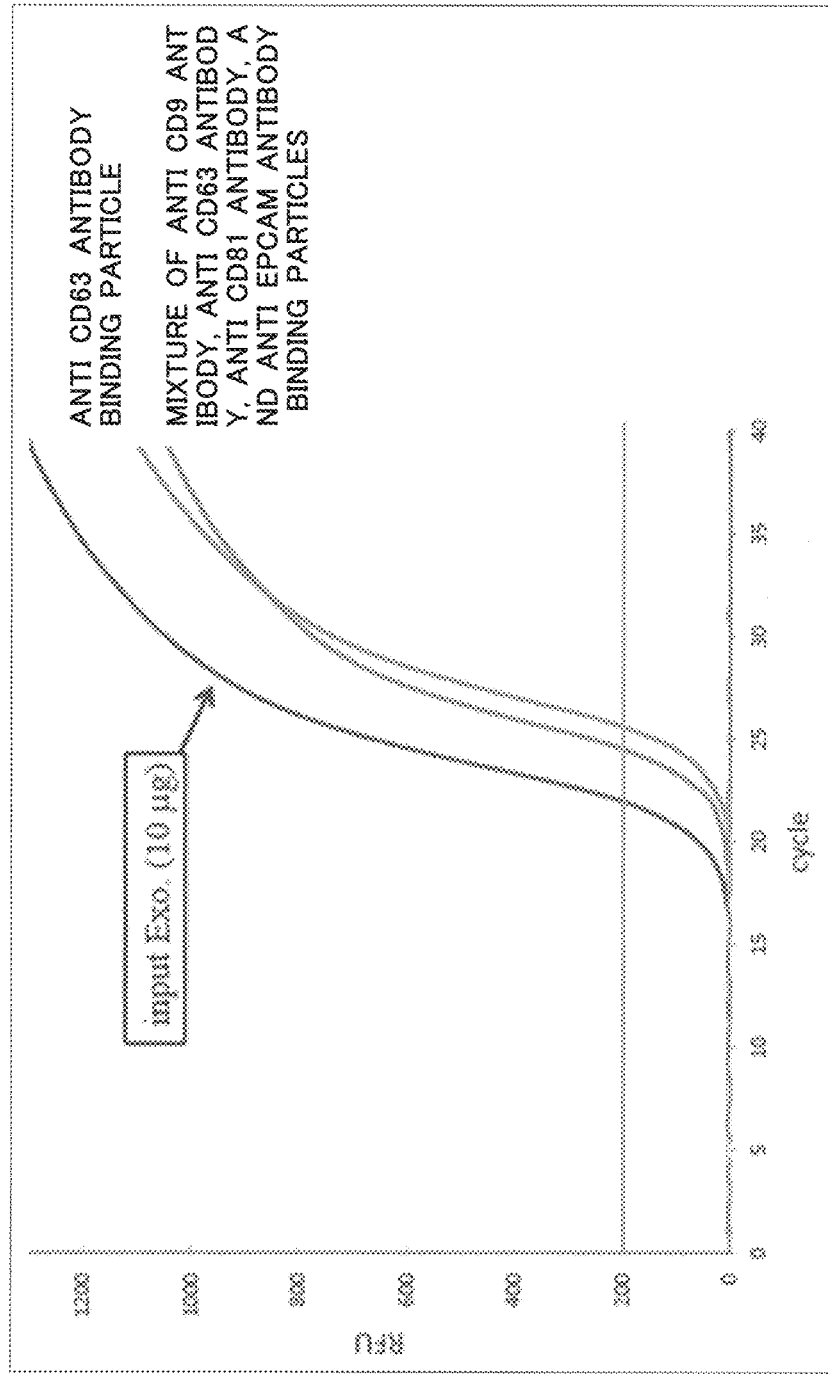
FIG. 8 is an amplification curve illustrating that microRNA can be quantified from the exosome that is captured by antibody binding magnetic particles.

As a result, an amplification curve as illustrated in FIG. 8 was acquired, and from the exosome captured by antibody binding magnetic particles, it was able to detect specific microRNA. Accordingly, by using the antibody binding magnetic particles, various microRNAs derived from a vesicle can be quantified, and based on profiling of them, it is possible to use them for determination of a disease.

Test Example 11—Detection of Protein Derived from Vesicle

Protein derived from a vesicle, which is present inside or on a surface of the vesicle, captured by antibody binding magnetic particles was detected by using Western blot analysis.

First, 100 μL of TBS (pH 7.4) containing 0.1% (w/v) magnetic particles (manufactured by JSR Life Sciences Corporation MS300/Carboxyl) that are bound with anti CD9 antibody, anti CD63 antibody, anti CD81 antibody or anti EpCAM antibody and 0.1% (w/v) nonionic surfactant (PLURONIC® F-68) and 0.1 mL of culture supernatant of HT29 cells (100 times the concentrated solution was diluted by a factor of 10 with TBS) containing exosome were added to a 1.5 mL tube followed by mixing.

The resultant was shaken for 1 hour at 25° C. After removal of the culture supernatant by magnetic collecting, it was washed 3 times with 0.5 mL of the washing buffer (TBS containing 0.1% (w/v) nonionic surfactant (PLURONIC® F-68)).

After discarding the washing solution by magnetic collecting, the antibody binding magnetic particles were suspended in 20 μL 1× sample buffer and allowed to stand for 5 minutes at 95° C. Meanwhile, detection of the surface protein (CD9, CD63, CD81, EpCAM) was performed by a non-reducing treatment and detection of the inside protein (Alix, Hsp70) was performed by a reducing treatment. The entire amount (20 μL) of each sample was applied and subjected to SDS-PAGE. The gel was transferred to a PVDF membrane, and then shaken for 2 hours at 37° C. with the blocking buffer (TBS containing 1% (w/v) BSA and 0.1% (w/v) TWEEN® 20). The resultant was washed with the washing buffer (TBS containing 0.10 (w/v) TWEEN® 20), and reacted with a primary antibody and a labeled antibody, each for 1 hour at 25° C.

For the detection of the protein other than Hsp70, anti CD9 antibody (manufactured by Abcam plc, ab2215), anti CD63 antibody (MX-49.129.5, Mouse IgG1, SantaCruz sc-5275), anti CD81 antibody (Clone M38, Abnova MAB6435), anti EpCAM antibody (manufactured by JSR Life Sciences Corporation), and anti Alix antibody (Alix (3A9) Mouse mAb, Cell signaling technology #2171S) were used as a primary antibody, and HRP labeled anti mouse IgG antibody (Mouse TRUEBLOT® ULTRA: Anti-Mouse IgG HRP, Rockland 18-8817-33) was used as a labeled antibody, respectively. Furthermore, for the detection of Hsp70, Anti-HSP70, Rabbit-Poly, with HRP Conjugated Secondary Antibody (manufactured by SBI, EXOAB-Hsp70A-1) was used.

When the reaction of the primary antibody and labeled antibody is completed, it was washed with the washing buffer (TBS containing 0.1% (w/v) TWEEN® 20), and reacted with a luminescent substrate (SUPERSIGNAL™ West Femto Maximum Sensitivity substrate, Thermo scientific Cat#34095). The Western bolt image was then analyzed by using a luminescence measuring device (LAS-3000, FUJIFILM). The results are illustrated in FIG. 9.

Figure 9:
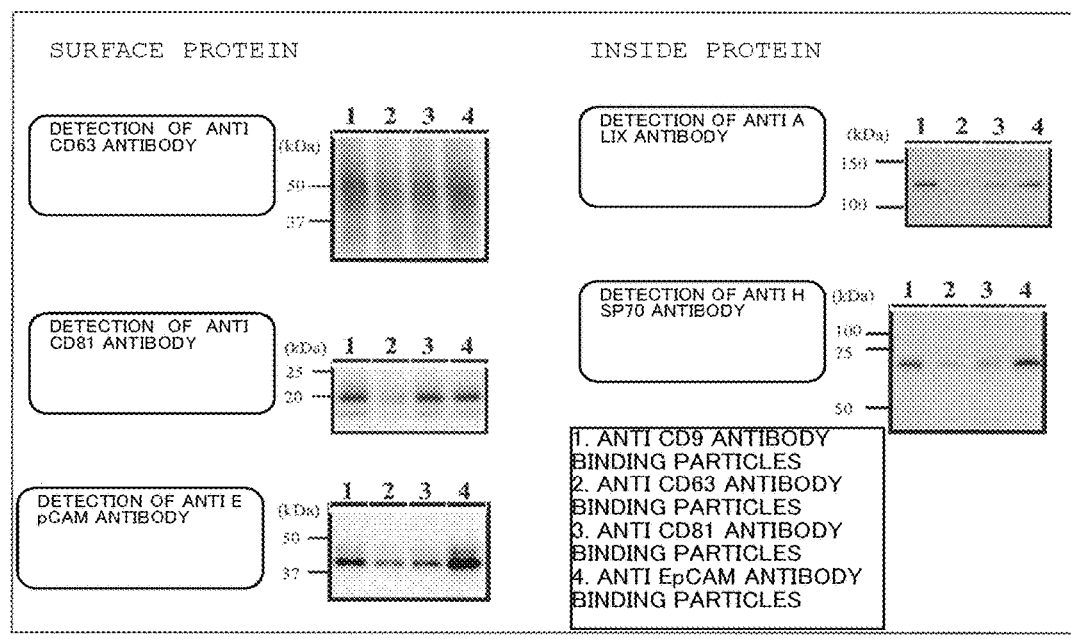
FIG. 9 is a Western blot image illustrating that the inside and surface proteins derived from a vesicle can be detected from a vesicle captured by antibody binding magnetic particles.

As a result, from the captured exosome in antibody binding magnetic particles, bands of the surface protein (CD9, CD63, CD81, EpCAM) and the inside protein (Alix, Hsp70) derived from a vesicle were detected with a desired size (FIG. 9).

Furthermore, the amount of the protein derived from a vesicle (surface protein CD9) was detected in the same manner as above, except that 0.1 mL of the culture supernatant of HT29 cells used for the above-mentioned reaction is changed to standard exosome (1, 3, 10 µg) or 1 mL of the culture supernatant of HT29 cells, respectively. The results obtained from a case in which anti CD9 antibody is used as a primary antibody are illustrated in FIG. 10.

Figure 10:
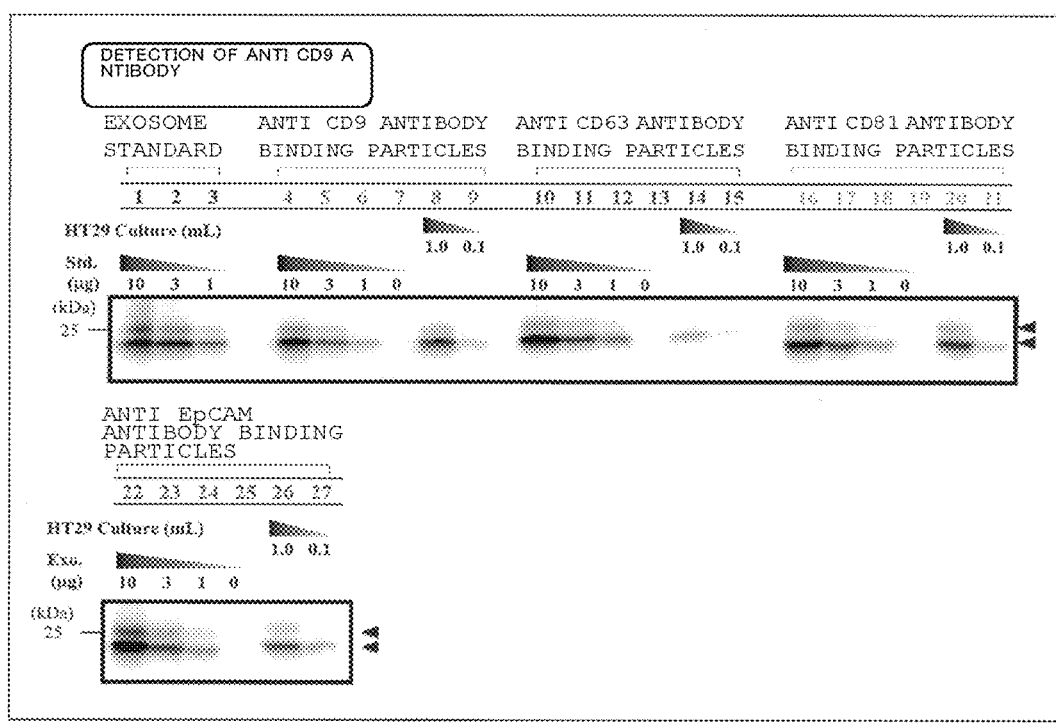
FIG. 10 is a Western blot image illustrating that the amount of vesicle captured by antibody binding magnetic particles is proportional to the amount of a vesicle which has been reacted.

As a result, it found that the detection amount of protein derived from a vesicle increases in proportion to the amount of standard exosome (1, 3, 10 µg) and liquid amount (0.1, 1 mL) of the culture supernatant which is used for the reaction (FIG. 10). Accordingly, it found that, by quantifying the protein derived from a vesicle, the amount of a vesicle in body fluid or culture supernatant can be measured.

Test Example 12—Detection of Vesicle from Body Fluid and Culture Supernatant

Protein derived from a vesicle in various cell culture supernatant and body fluid (blood serum, blood plasma, and urine) was detected by using Western blot method. As for the blood serum, 3 test samples of blood serum of a healthy person (Serum A, Serum B, Serum C) were used, and as for the blood plasma, 3 test samples of heparin blood plasma of a healthy person (Plasma (Heparin) A, Plasma (Heparin) B, Plasma (Heparin) C) were used, respectively. Furthermore, as for the urine, 3 test samples of urine of a healthy person (Urine D, Urine E, Urine F) were used. Specific order is described in the following.

First, (i) 100 µL of TBS (pH 7.4) containing 0.1% (w/v) magnetic particles (manufactured by JSR Life Sciences Corporation MS300/Carboxyl) bound with anti CD9 antibody, anti CD63 antibody, anti CD81 antibody, or anti EpCAM antibody and 0.1% (w/v) nonionic surfactant (PLURONIC® F-68) and (ii) 100 µL of cell culture supernatant (HT-29, 293T or NCI-H520) or body fluid derived from a healthy person (blood serum, blood plasma, or urine (3 test samples for each)) were added to a 1.5 mL tube followed by mixing.

The resultant was shaken for 20 minutes at 25° C. After removal of the unreacted solution by magnetic collecting, it was washed 3 times with 0.5 mL of the washing buffer (TBS containing 0.1% (w/v) nonionic surfactant (PLURONIC® F-68)).

Subsequently, after discarding the washing solution by magnetic collecting, the antibody binding magnetic particles were suspended in 20 µL 1× sample buffer and allowed to stand for 5 minutes at 95° C. The entire amount (20 µL) was applied and subjected to SDS-PAGE. The gel was transferred to a PVDF membrane, and then shaken for 2 hours at 37° C. with the blocking buffer (TBS containing 1% (w/v) BSA and 0.1% (w/v) TWEEN® 20). The resultant was washed with the washing buffer (TBS containing 0.1% (w/v) TWEEN® 20).

It was then reacted with anti CD9 antibody as a primary antibody and HRP labeled anti mouse IgG antibody (Mouse TRUEBLOT® ULTRA: Anti-Mouse IgG HRP, Rockland 18-8817-33) as a labeled antibody, each for 1 hour at 25° C. It was subsequently washed with the washing buffer (TBS containing 0.1% (w/v) TWEEN® 20), and reacted with a luminescent substrate. The Western bolt image was then determined by using a luminescence measuring device (LAS-3000, FUJIFILM). The results are illustrated in FIG. 11.

As a result, in the magnetic particles bound with anti CD9 antibody, anti CD63 antibody, or anti CD81 antibody, the surface protein derived from a vesicle (CD9), which has been captured from all of the culture supernatants or body fluids, was detected (FIG. 11). Meanwhile, in the magnetic particles bound with anti EpCAM antibody, the surface protein derived from a vesicle (CD9) was detected from the culture supernatant of HT29 and NCI-H520 of the EpCAM-producing cell. However, from the 293T of EpCAM-not producing cells and body fluid from every healthy person (blood serum, blood plasma, and urine), the surface protein derived from a vesicle (CD9) was not detected (FIG. 11).

Accordingly, by using a particle which is bound with a ligand against an antigen derived from a disease such as cancer marker, vesicles derived from a healthy person or a person with a disease can be separated from each other and can be detected. Therefore, if the signal intensity of a biological sample derived from a test subject is compared to the signal intensity of a biological sample derived from a healthy person, onset of a disease in a test subject can be determined.

Test Example 13—Detection of Vesicle by ELISA

Signal intensity derived from a vesicle was detected quantitatively by using an ELISA method. Specific procedure is described in the following.

To a 96 well white plate (manufactured by Corning Incorporated), TBS (pH 7.4) containing 0.1% (w/v) magnetic particles (manufactured by JSR Life Sciences Corporation MS300/Carboxyl) that are bound with anti CD9 antibody, anti CD63 antibody, anti CD81 antibody or anti EpCAM antibody and 0.1% (w/v) nonionic surfactant (PLURONIC® F-68), and culture supernatant of cells (293T, NCI-H520, HT29, or 22Rv-1) were added, each in amount of 25 µL, followed by mixing. The resultant was shaken for 20 minutes at 25° C., and while conducting magnetic collecting, the antibody binding magnetic particles after the reaction were washed with the washing buffer (TBS containing 0.01% (w/v) TWEEN® 20). After removal of the washing buffer while conducting magnetic collecting, 50 µL of MES solution (0.5 µg/mL) of an antibody, that is, anti CD9 antibody or anti CD81 antibody labeled with alkali phosphatase, was added thereto. It was shaken for 20 minutes at 25° C., and while conducting magnetic collecting, the antibody binding magnetic particles after the reaction were washed with the washing buffer (TBS containing 0.01% (w/v) TWEEN® 20). Then, 50 μL of a luminescent substrate (LUMIPULSE® substrate solution, manufactured by FUJIREBIO INC.) was added thereto, and after 5 minutes, the luminescence intensity was measured by using a luminescence measuring device (GLOMAX®, manufactured by Promega).

After that, the signal intensity of a vesicle derived from cancer cells (NCI-H520, HT29, 22Rv-1) was compared to the signal intensity of a vesicle derived from 293T cells. The results are shown in Table 5 and 6.

As a result, in the magnetic particles bound with anti CD9 antibody, anti CD63 antibody, or anti CD81 antibody, it found that the signal intensity of an extracellular vesicle of cancer cells was close to the signal intensity of an extracellular vesicle of 293T cells, for both the detection using ALP labeled anti CD9 antibody (Table 5) and detection using ALP labeled anti CD81 antibody (Table 6). Meanwhile, in the magnetic particles bound with anti EpCAM antibody, the signal intensity of an extracellular vesicle of cancer cells was remarkably higher than the signal intensity of an extracellular vesicle of 293T cells.

Furthermore, the ratio of exosome captured by the magnetic particles bound with anti CD9 antibody, anti CD63 antibody, or anti CD81 antibody varies, depending on the type of cancer cells, for example, the capturing rate is high for the magnetic particles bound with anti CD81 antibody of an extracellular vesicle of NCI-H520 cells (Table 5 and Table 6).

For such reasons, by using particles bound with a ligand against an antigen derived from a disease such as a common marker protein derived from a vesicle (for example, CD9, CD63, or CD81), or a cancer marker (EpCAM), vesicles derived from a healthy person and a person with a disease can be separated from each other and can be detected quantitatively by using an ELISA method or the like. Accordingly, when the signal intensity of a biological sample derived from a test subject is compared to the signal intensity of a biological sample derived from a healthy person, onset of a disease in a test subject can be determined.

Furthermore, by detecting and comparing the signal intensity of a vesicle with the same method as above from a biological sample derived from a test subject before and after the administration of a drug for treating disease, the drug efficacy of a drug for treating a disease can be evaluated.

TABLE 5

Comparison of signal intensity using ALP labeled CD9 antibody (/293T derived-vesicle)

| Cell name | Origin | Antibody binding magnetic particles | | | |
|---|---|---|---|---|---|
| | | Anti CD9 antibody | Anti CD63 antibody | Anti CD81 antibody | Anti EpCAM antibody |
| 293T | Fetal kidney cell | 1.0 | 1.0 | 1.0 | 1.0 |
| NCI-H520 | Lung cancer cell | 3.1 | 0.4 | 1.2 | 338.5 |
| HT29 | Colon adeno-carcinoma | 1.7 | 0.7 | 0.6 | 389.1 |
| 22Rv-1 | Prostate cancer | 1.8 | 0.8 | 0.8 | 202.9 |

TABLE 6

Comparison of signal intensity using ALP labeled CD81 antibody (/293T derived-vesicle)

| Cell name | Origin | Antibody binding magnetic particles | | | |
|---|---|---|---|---|---|
| | | Anti CD9 antibody | Anti CD63 antibody | Anti CD81 antibody | Anti EpCAM antibody |
| 293T | Fetal kidney cell | 1.0 | 1.0 | 1.0 | 1.0 |
| NCI-H520 | Lung cancer cell | 0.5 | 0.2 | 0.5 | 132.6 |
| HT29 | Colon adeno-carcinoma | 0.2 | 0.1 | 0.1 | 76.5 |
| 22Rv-1 | Prostate cancer | 0.3 | 0.2 | 0.1 | 41.0 |

The invention claimed is:

1. A method for separating a vesicle having a lipid bilayer membrane from a biological sample, the method comprising:
    forming a complex of a vesicle and a solid phase carrier by bringing the biological sample comprising the vesicle having the lipid bilayer membrane into contact with the solid phase carrier to which a ligand for recognizing a surface antigen present on a surface of the vesicle and is bound, and
    washing the complex,
    wherein the forming and the washing is performed in the presence of a nonionic surfactant to reduce an aggregation of the complex,
    wherein the nonionic surfactant is one or more selected from the group consisting of a polyalkylene glycol ethylene oxide adduct, a fatty acid ester of sorbitan, a fatty acid ester of sorbitol, an ethylene oxide adduct of sorbitan fatty acid ester, and an ethylene oxide adduct of sorbitol fatty acid ester.

2. The method according to claim 1, wherein the nonionic surfactant is a block copolymer of a polyalkylene glycol ethylene oxide adduct.

3. The method according to claim 1, wherein the nonionic surfactant is a block copolymer comprising a block formed of a polyethylene oxide and a block formed of a polyalkylene oxide and having 3 or more carbon atoms in the alkylene.

4. The method according to claim 1, wherein the biological sample is a body fluid or a cell culture supernatant.

5. The method according to claim 1, wherein the vesicle is an exosome.

6. The method according to claim 1, wherein the surface antigen is an antigen protein present on a surface of an exosome and the ligand is an antibody which recognizes the antigen protein.

7. The method according to claim 1, wherein the solid phase carrier is a magnetic particle.

8. The method according to claim 7, wherein the washing comprises:
    collecting the magnetic particle by magnetic force to separate the magnetic particle from a liquid phase, and
    dispersing the magnetic particle that is separated by the collecting in a washing solution.

* * * * *